(12) United States Patent
Shin et al.

(10) Patent No.: US 6,598,465 B2
(45) Date of Patent: *Jul. 29, 2003

(54) ELECTRORHEOLOGICAL AND MAGNETORHEOLOGICAL FLUID SCANNING RHEOMETER

(75) Inventors: Seyhun Shin, Bryn Mawr, PA (US); Young Cho, Cherry Hill, NJ (US); Kenneth Kensey, Malvern, PA (US); William N. Hogenauer, Gilbertsville, PA (US); Sangho Kim, Philadelphia, PA (US)

(73) Assignee: Rheologics, Inc., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/186,736

(22) Filed: Jul. 1, 2002

(65) Prior Publication Data

US 2003/0066341 A1 Apr. 10, 2003

Related U.S. Application Data

(63) Continuation of application No. 09/722,954, filed on Nov. 27, 2000, now Pat. No. 6,484,566, which is a continuation-in-part of application No. 09/573,267, filed on May 18, 2000, now Pat. No. 6,402,703.
(60) Provisional application No. 60/227,759, filed on Aug. 25, 2000.

(51) Int. Cl.[7] .............................................. G01N 11/43
(52) U.S. Cl. ....................... 73/54; 324/71.1; 73/54.01; 73/54.14
(58) Field of Search ...................... 73/54.01, 54.07, 73/54.14; 324/71.1, 204, 214

(56) References Cited

U.S. PATENT DOCUMENTS 1,810,992 A    6/1931  Dallwitz-Wegner
2,149,847 A *  3/1939  Kolin ...................... 73/861.13
2,343,061 A    2/1944  Irany (List continued on next page.)

FOREIGN PATENT DOCUMENTS

| DE | 31 38 514 A1 | 4/1983 |
| EP | 0 654 286 A1 | 12/1994 |
| FR | 2 510 257 | 1/1983 |

(List continued on next page.)

OTHER PUBLICATIONS

Kensey, et al., Effects of Whole Blood Viscosity on Atherogenesis—J. of Invasive Cardiology V. 9, 17, 1997.

(List continued on next page.)

*Primary Examiner*—Edward Lefkowitz
*Assistant Examiner*—Michael Cygan
(74) *Attorney, Agent, or Firm*—Caesar, Rivise, Bernstein, Cohen & Pokotilow, Ltd.

(57) ABSTRACT

A scanning rheometer is presented for the rheological property measurement of electrorheological (ER) and magnetorheological (MR) fluids using a non-linear viscoplastic model, based on the fluid height variation with respect to time. The rheometer basically includes a static (e.g., an overhead reservoir) or a dynamic source of fluid, a channel or slit whose sides form electrodes which are in contact with the flowing ER fluid, or a capillary tube exposed to a static/alternating magnetic field for flowing MR fluids, a transfer tube, either one or two riser tubes, and a column level detector for monitoring the column of fluid as it moves in one of the riser tubes. The column level detector is coupled to a processor which analyzes, among other things, column height vs. time data to determine both viscosity and yield stress. The rheometer overcomes one of the major drawbacks of the conventional rheometer: the inability to produce the yield stress of the ER, or MR, fluid in an absolute zero shear rate range. The results with this rheometer are compared with those obtained from a commercially-available rheometer which indicates excellent agreement.

12 Claims, 17 Drawing Sheets

U.S. PATENT DOCUMENTS

| | | |
|---|---|---|
| 2,696,734 A | 12/1954 | Brunstrum et al. |
| 2,700,891 A | 2/1955 | Shafer |
| 2,934,944 A | 5/1960 | Eolkin |
| 3,071,961 A | 1/1963 | Heigl et al. |
| 3,116,630 A | 1/1964 | Piros |
| 3,137,161 A | 6/1964 | Lewis et al |
| 3,138,950 A | 6/1964 | Welty et al. |
| 3,277,694 A | 10/1966 | Cannon et al. |
| 3,286,511 A | 11/1966 | Harkness |
| 3,342,063 A | 9/1967 | Smythe et al. |
| 3,435,665 A | 4/1969 | Tzentis |
| 3,520,179 A | 7/1970 | Reed |
| 3,604,247 A | 9/1971 | Gramain et al. |
| 3,666,999 A | 5/1972 | Moreland, Jr. et al. |
| 3,680,362 A | 8/1972 | Geerdes et al. |
| 3,699,804 A | 10/1972 | Gassmann et al. |
| 3,713,328 A | 1/1973 | Aritomi |
| 3,720,097 A | 3/1973 | Kron |
| 3,782,173 A | 1/1974 | Van Vessem et al. |
| 3,839,901 A | 10/1974 | Finkle et al. |
| 3,853,121 A | 12/1974 | Mizrachy et al. |
| 3,864,962 A | 2/1975 | Stark et al. |
| 3,908,441 A | 9/1975 | Virloget |
| 3,911,728 A | 10/1975 | Fixot |
| 3,952,577 A | 4/1976 | Hayes et al. |
| 3,967,934 A | 7/1976 | Seitz et al. |
| 3,990,295 A | 11/1976 | Renovanz et al. |
| 3,999,538 A | 12/1976 | Philpot, Jr. |
| 4,083,363 A | 4/1978 | Philpot, Jr. |
| 4,149,405 A | 4/1979 | Ringrose |
| 4,165,632 A | 8/1979 | Weber et al. |
| 4,193,293 A | 3/1980 | Cavallari |
| 4,207,870 A | 6/1980 | Eldridge |
| 4,302,965 A | 12/1981 | Johnson et al. |
| 4,341,111 A | 7/1982 | Husar |
| 4,417,584 A | 11/1983 | Cathignol et al. |
| 4,426,878 A | 1/1984 | Price et al. |
| 4,432,761 A | 2/1984 | Dawe |
| 4,461,830 A | 7/1984 | Philpot, Jr. |
| 4,517,830 A | 5/1985 | Gunn, deceased et al. |
| 4,519,239 A | 5/1985 | Kiesewetter et al. |
| 4,554,821 A | 11/1985 | Kiesewetter et al. |
| H93 H | 7/1986 | Matta et al. |
| 4,616,503 A | 10/1986 | Plungis et al. |
| 4,637,250 A | 1/1987 | Irvine, Jr. et al. |
| 4,643,021 A | 2/1987 | Mattout |
| 4,680,957 A | 7/1987 | Dodd |
| 4,680,958 A | 7/1987 | Ruelle et al. |
| 4,750,351 A | 6/1988 | Ball |
| 4,856,322 A | 8/1989 | Langrick et al. |
| 4,858,127 A | 8/1989 | Kron et al. |
| 4,884,577 A | 12/1989 | Merrill |
| 4,896,752 A | 1/1990 | Shtarkman |
| 4,899,575 A | 2/1990 | Chu et al. |
| 4,909,489 A | 3/1990 | Doi |
| 4,928,935 A | 5/1990 | Matsui |
| 4,947,678 A | 8/1990 | Hori et al. |
| 5,015,926 A | 5/1991 | Casler |
| 5,088,703 A | 2/1992 | Takano et al. |
| 5,099,698 A | 3/1992 | Kath et al. |
| 5,170,866 A | 12/1992 | Ghaem |
| 5,181,415 A | 1/1993 | Esvan et al. |
| 5,222,497 A | 6/1993 | Ono |
| 5,244,375 A | 9/1993 | Laurence et al. |
| 5,257,529 A | 11/1993 | Taniguchi et al. |
| 5,259,487 A | 11/1993 | Petek |
| 5,271,398 A | 12/1993 | Schlain et al. |
| 5,322,484 A | 6/1994 | Reuter |
| 5,327,778 A | 7/1994 | Park |
| 5,333,497 A * | 8/1994 | Br nd Dag A. et al. ...... 73/219 |
| 5,353,897 A | 10/1994 | Woessner |
| 5,354,489 A | 10/1994 | Inoue et al. |
| 5,358,084 A | 10/1994 | Schramm |
| 5,365,776 A | 11/1994 | Lehmann et al. |
| 5,417,314 A | 5/1995 | Sproston et al. |
| 5,421,328 A | 6/1995 | Bedingham et al. |
| 5,443,078 A | 8/1995 | Uflacker |
| 5,447,440 A | 9/1995 | Davis et al. |
| 5,477,946 A | 12/1995 | Kawamata et al. |
| 5,491,408 A | 2/1996 | Rousseau |
| 5,494,639 A | 2/1996 | Grzegorzewski |
| 5,516,445 A | 5/1996 | Sasaki et al. |
| 5,522,481 A | 6/1996 | Watanabe |
| 5,569,432 A | 10/1996 | Maciejewski |
| 5,590,745 A | 1/1997 | Rensel et al. |
| 5,601,164 A | 2/1997 | Ohsaki et al. |
| 5,607,996 A | 3/1997 | Nichols et al. |
| 5,629,209 A | 5/1997 | Braun, Sr. et al. |
| 5,686,659 A | 11/1997 | Neel et al. |
| 5,725,563 A | 3/1998 | Klotz |
| 5,792,660 A | 8/1998 | Spillert et al. |
| 5,810,696 A | 9/1998 | Webb |
| 5,837,885 A | 11/1998 | Goodbread et al. |
| 5,988,336 A | 11/1999 | Wendt et al. |
| 5,992,582 A | 11/1999 | Lou et al. |
| 5,993,358 A | 11/1999 | Gureghian et al. |
| 6,019,735 A | 2/2000 | Kensey et al. |
| 6,039,078 A | 3/2000 | Tamari |
| 6,077,234 A * | 6/2000 | Kensey ...................... 600/573 |
| 6,082,715 A | 7/2000 | Vandermolen |
| 6,152,888 A | 11/2000 | Kensey et al. |
| 6,159,396 A * | 12/2000 | Fujita et al. ................. 252/572 |
| 6,193,677 B1 | 2/2001 | Cady |
| 6,200,277 B1 | 3/2001 | Kensey |
| 6,261,244 B1 | 7/2001 | Kensey et al. |
| 6,322,524 B1 | 11/2001 | Kensey et al. |
| 6,322,525 B1 | 11/2001 | Kensey et al. |
| 6,402,703 B1 | 6/2002 | Kensey et al. |
| 6,412,336 B2 | 7/2002 | Shin et al. |
| 6,428,488 B1 | 8/2002 | Kensey et al. |
| 6,484,566 B1 * | 11/2002 | Shin et al. .................. 73/54.07 |

FOREIGN PATENT DOCUMENTS

| | | | |
|---|---|---|---|
| JP | 401203941 A | | 8/1989 |
| WO | WO-92/00469 | * | 6/1991 |
| WO | WO92/00469 | | 1/1992 |
| WO | WO 92/15878 | | 9/1992 |
| WO | WO 94/20832 | | 9/1994 |
| WO | WO 99/10724 | | 3/1999 |

OTHER PUBLICATIONS

Leonhardt, et al., Studies of Plasma Viscosity in Primary Hyperlipoproteinaemia—Athersclerosis, V. 28, 29–40, 1977.

Ernst, et al., Cardiovascular Risk Factors and Hemorheology: Physical fitness, Stress & Obesity—Atherosclerosis V. 59, 263–269, 1986.

Levenson, et al., Cigarette Smoking & Hypertension—Atherosclerosis V. 7, 572–577, 1987.

Rillaerts, et al., Blood Viscosity in Human Obesity; relation to glucose Tolerance & Insulin Status—Int'l Jrnl of Obesity, V. 13, 739–741, 1989.

Rosenson, R., Viscosity & Ischemic Heart Disease—Jrnl of Vascular Medicine & Biology, V. 4, 206–212, 1993.

Letcher, et al., Direct Relationship between Blood Pressure & Blood Viscosity in Normal and Hypertensive Subjects—Amer. Jrnl of Medicine, V.70, 1195–1203, Jun. 1981.

Zwick, K.J., The Fluid Mechanics of Bonding With Yield Stress Exposies, Dissortation—Univ of Penna, PA, USA, 1–142, 1996.

Yarnell, et al., Fibrinogen, Viscosity, & White Blood Cell Count Are Major Risk Factors for Ischemic Heart Disease—Circulation, V. 83, No. 3, Mar., 1991.

Tangney, et al., Postprandial changes in Plasma and Serum Viscosity and Plasma Lipids and Lipoproteins After an Acute Test Meal—Amer. Jrnl. Of Clinical Nutrition, V.65, pp. 36–40, 1997.

Seplowitz, et al., Effects of Lipoproteins on Plasma Viscosity—Atherosclerosis, V. 38, pp. 89–95, 1981.

Rosenson, et al., Hyperviscosity Syndrome in Hypercholesterolemic Patient with Primary Biliary Cirrhosis—Gastroenterology, V. 98, No. 5, 1990.

Lowe, et al., Blood Viscosity & Risk of Cardiovascular Events: Edinburgh Artery Study British Jrnl of Haematology, V. 96, 168–173, 1997.

Koenig, W., Blood Rheology Assoc. With Cardiovascular Risk Factors & Chronic Cardiovascular Disease; Results of Epidemiologic Cross–sectional Study—Am. Coll. Angiology, Paradise Is., Bahamas—Oct. 1987.

Hell, K., Importance of Blood Visco–elasticity in Arterosclerosis Internl Coll of Angiology, Montreaux, Switzerland, Jul. 1987.

Delaunois, A., Thermal method for Continuous Blood Velocity Measurements in Large Blood Vessels, and Cardiac Output Determination—Med & Biol. Engineering, Mar. 1973, vol. 11, 201–205.

Nerem, et al., Fluid Mechanics in Atherosclerosis—Handbook of Bioengineering, Chap. 21, 20.24 to 21.22.

Litt, et al., Theory & Design of Disposable Clinical Blood Viscometer—Biorheology, vol. 25, 697–712, 1988.

Cooke, et al., Automated Measurement of Plasma Viscosity by Capillary Viscometer—J. Clinical Pathology, vol. 31, 1213–1216, 1988.

Jiminez, et al., A Novel Computerized Viscometer/Rheometer—Rev. Sci. Instru. vol. 65 (1), pp. 229–241, Jan. 1994.

Harkness, A New Instrument for the Measurement of Plasma–Viscosity—The Lancet, New Inventions, pp. 280–281, Aug. 10, 1963.

Pringle, et al., Blood Viscosity & Raynaud's Disease—The Lancet, May 1965.

Walker, et al., Measurement of Blood.

Oguraa, et al., Measurement of Human Red Blood Cell Deformability using a Single Micropore on a Thin Si3N4 Film, IEEE Transactions on Biomedical Engineering, V. 38, No. 9, Aug. 1991.

Hausler, et al., A Newly Designed Oscillating Viscometer for Blood Viscosity Measurements, 1999 V. 33, No. 4, Biorheology, p. 397–404.

Martin, et al., Apparent Viscosity of Whole Human Blood at Various Hydrostatic Pressure I. Studies on Anticoagulated Blood Employing new Capillary Viscometer, Biorheology 3–12, V. 11, 1978.

Rheinhardt, et al., Rheologic Measurements on Small Samples with a New Capillary Viscometer, J.Lab. And Clin. Med., 921–931, Dec. 1984.

Chmiel, A New Capillary Viscometer for Clinical use, Biorhelolgy, 301–307, V. 12, 1979.

Pall Corporation, Pall BPF4 High Efficiency Leukocyte Removal Blood Processing Filter System, Pall Biomedical Products Corporation 1993.

Qamar, et al., The Goldman Algorithm Revisited:Prospective E#valuation of Computer Derived Algorithm Vs. Unaided Physician Judgement in Suspected Acute Myocardial Inf., AM. Hrt J. 138, V. 4, 705–709, 1999.

Leonhardt, et al., Studies of Plasma Viscosity in Primary Hyperlipoproteinaemia, Atherosclerosis, V.28, 29–40, 1977.

* cited by examiner

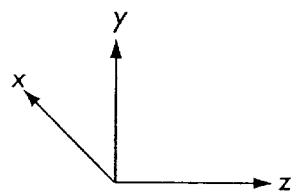
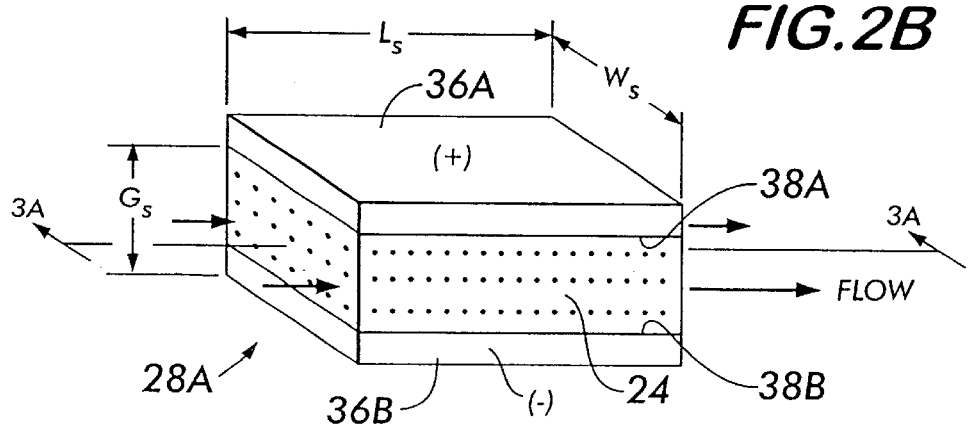
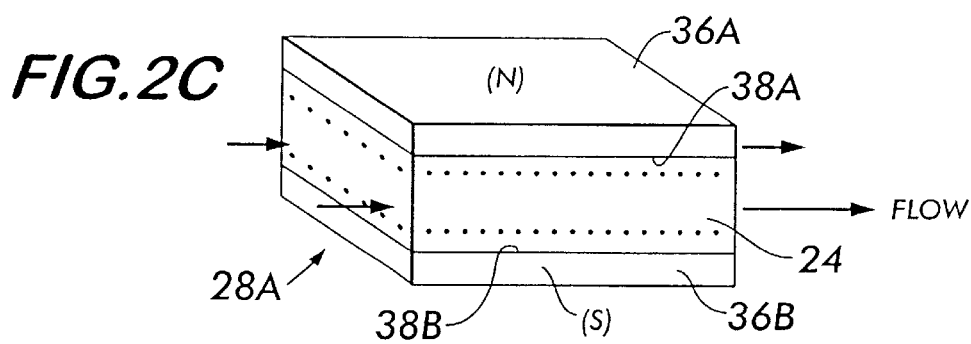
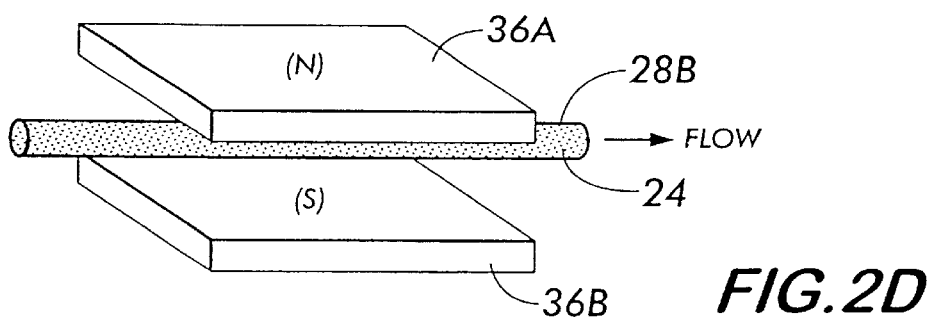

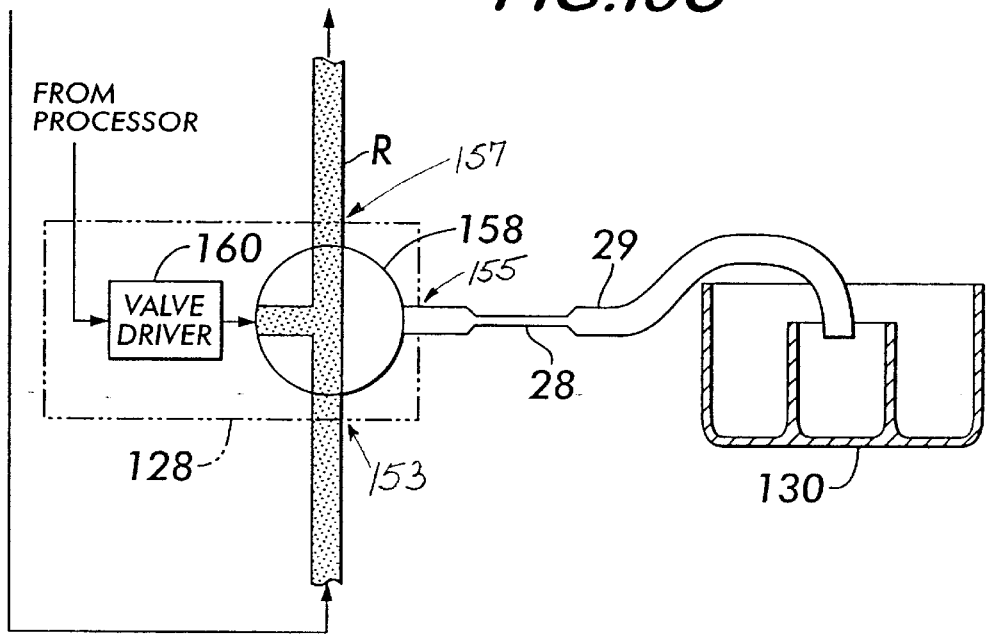
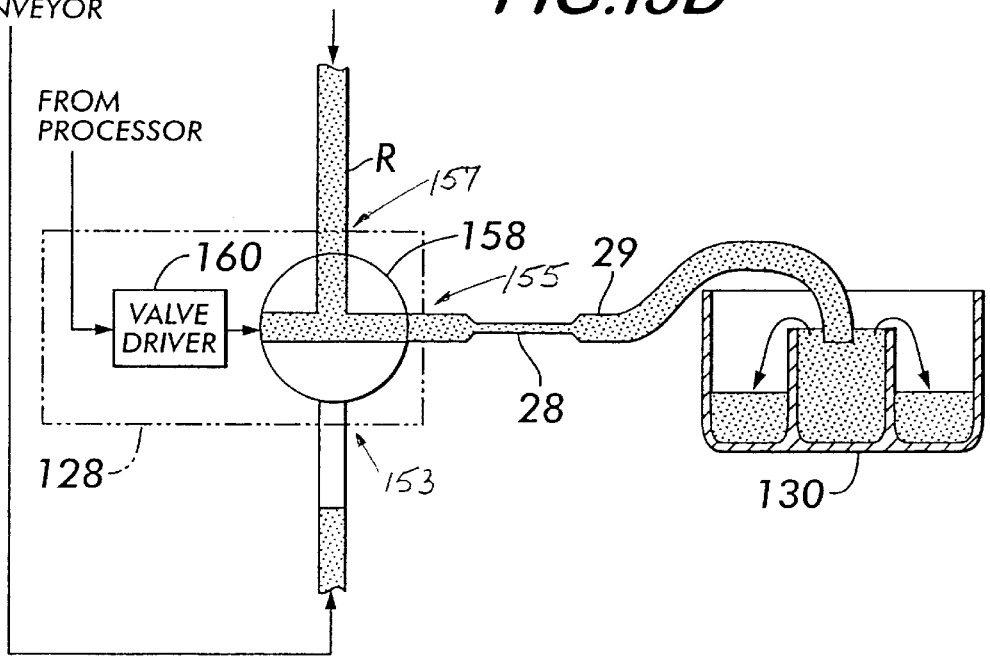

ELECTRORHEOLOGICAL AND MAGNETORHEOLOGICAL FLUID SCANNING RHEOMETER

RELATED APPLICATIONS

This application is a continuation application of application Ser. No. 09/722,954, (now U.S. Pat. No. 6,484,566) filed on Nov. 27, 2000, entitled ELECTROREOLOGICAL AND MAGNETORHEOLOGICAL FLUID SCANNING RHEOMETER, which in turn is based on a provisional Application Serial No. 60/227,759 filed Aug. 25, 2000 entitled ELECTRORHOLOGICAL FLUID SCANNING VISCOMETER, and is also a Continuation-in-Part of application Ser. No. 09/573,267, filed May 18, 2000 (now U.S. Pat. No. 6,402,703 (Kensey et al.)) entitles DUAL RISER/SINGLE CAPILLARY VISCOMETER, and all of whose entire disclosures are incorporated by reference herein.

SPECIFICATION

FIELD OF THE INVENTION

The invention pertains to electrorheological (ER) and magnetorheologocial (MR) fluid devices, and more particularly, to a device for changing the viscosity and yield stress of ER and MR fluids and for measuring the change in those parameters.

BACKGROUND OF INVENTION

An electrorheological (ER) fluid is typically a suspension of solid particles in dielectric carrier liquids that undergo a rapid and reversible viscosity transition upon the application of electric fields. This dramatic transition of viscosity is often referred to as the ER effect or sometimes the "Winslow effect," after Willis Winslow (1949) who first reported the phenomenon. The ER effect has not been fully understood but can be described as follows: the external electric field induces electric polarization within each particle relative to the carrier liquid (an electric dipole), and the resulting electrostatic interaction forces between the particles lead to the formation of aggregates aligned in the direction of the field. The presence of these particles aggregates in the flow field causes an increase in the fluid viscosity and a decrease in flow rate. During the past two decades, the ER-related investigations have increased due to the potential applications of the special properties of the ER fluids for the performance improvement of devices such as engine mounts, clutches, brakes, and shock absorbers; for examples, see U.S. Pat. No. 5,088,703 (Takano et al.); U.S. Pat. No. 6,082,715 (Vandermolen); U.S. Pat. No. 5,988,336 (Wendt et al.); U.S. Pat. No. 5,358,084 (Schramm); and U.S. Pat. No. 5,322,484 (Reuter).

Numerous experiments show that ER-fluids are generally visco-plastic fluids. Various rheological models have been proposed (e.g., R. B. Bird, R. C. Amstrong and O. Hassager, "Dynamics of Polymeric Liquids", Vol. 1, *Fluid Mechanics*, Wiley 1987), and the most often used model under shearing deformation is the Bingham plastic model (also referred to as "linear viscoplastic model"), where the shear stress is given by:

$$\tau = \tau_0 + \mu_B \dot{\gamma} \quad (1)$$

where $\dot{\gamma}$ is the shear rate, $\mu_B$ is the constant Bingham viscosity and $\tau_0$ is the yield stress induced by the electric field. However, it has been found that yielded ER-fluids may experience shear thinning, i.e., its viscosity decreases gradually with the increase of shear rate. This is probably because the destruction of the internal structure responsible for the yield behavior is a gradual process, during which the resistance to deformation becomes weaker, and is not completed until a high shear stress level is reached. Therefore, the Bingham plastic model may overestimate the true yield stress significantly due to the shear thinning at low shear rates. Wan 1982; O'Brien & Julien 1988.

A Herschel-Bulkley rheological model (also referred to as a non-linear viscoplastic model) seems to be more appropriate in depicting the ER-fluid behavior. This rheological model is empirical, nonetheless the results predicted using this model are often accurate over a wide range of shear rates and are reproducible. The key feature of this rheological model is that when the applied stress is smaller than the yield stress, there is no flow; the material supports a finite stress elastically without flow. For the Herschel-Bulkley model, the elastic strains are taken to be small such that the material is considered to be rigid. Once the applied stress exceeds the yield stress of the material, there is a transition from elastic to plastic behavior and the material behaves like a power-law fluid. This behavior can be interpreted to the microstructure of the fluid; for instance, in some ER fluids under a static/alternating electric field, it is found that electrostatic interactions between the dispersed particles lead to a chain-like structure, indicating a yield stress of the ER fluid. Substantial stresses may be required to break down this structure; the ER fluid will then flow. When the stresses are removed, the chain-like structure reforms.

In simple shear, the constitutive equations for the Herschel-Bulkley fluid are as follows:

$$\dot{\gamma}=0 \leftarrow \rightarrow \tau < \tau_0 \dot{\gamma} > 0 \leftarrow \rightarrow \tau = \tau_0 + K\dot{\gamma}^n \quad (2)$$

where $\tau_0$ is a yield stress, K is a flow consistency, and n is a flow index ranging from 0 to 1 for shear thinning fluid. The upper limit where n=1 corresponds to a Bingham plastic fluid, and K becomes the regular dynamic constant viscosity. It has been shown that $\tau_0$, i.e., the yield stress increases with the applied electricfield strength (E) as $\tau_0$ $E^{\alpha}$, where $\alpha$ assumes values close to 2 for low to moderate field strengths, but often appears to fall below 2 for higher E fields. In this rheological model, the yield stress, the fluid consistency, the flow index which are often referred to as the Herschel-Bulkley parameters should be determined from the measurement.

Much of the same discussion also applies to magnetorheological (MR) fluids except that magnetic fields (B) are applied to the MR field rather than a static/alternating electric fields. An MR fluid is typically a suspension of solid particles in diamagnetic liquids that undergo a rapid and reversible viscosity transition upon the application of magnetic fields. This dramatic transition of viscosity is often referred to as the MR effect. In addition, although it has been shown that yield stress increases with the applied magnetic field strength (B) as $\tau_0$ $B^{\alpha}$, the range for a is not necessarily close to 2 for low to moderate field strengths, or below 2 for higher field strengths, as is the case for ER fluids, as mentioned previously.

There exist several flow-measuring devices (i.e., rheometers) to measure the ER or MR properties. Those rheometers can be classified into three types: 1) capillary tube type, 2) rotating cylinder type, and 3) falling ball/needle type.1–2 These rheometers produce ER/MR-property data (shear stress etc.,) at a shear rate at a time. Thus, in order to measure the ER/MR property over a range of shear rates, it is necessary to repeat the measurement by varying shear rates. In order to cover a range of shear rates, it is necessary to vary pressure, rotating speed, or the density of the falling object. Such operations make an ER/MR-property measurement system complicated and labor intensive. Therefore, there is a need to develop a new rheometer for ER and MR fluids that is simple and accurate.

In U.S. Pat. No. 6,019,735 (Kensey et al.), which is assigned to the same Assignee, namely Visco Technologies, Inc., of the present invention, there is disclosed a scanning-capillary-tube viscometer for measuring the viscosity of a fluid, e.g., circulating blood of a living being. One of the important features of the scanning-capillary viscometer is that both flow rate and pressure drop at a capillary tube can be determined by fluid level variation with time in a U-type tube system, with a only single fluid level variation measurement required for Newtonian fluids, and a range of fluid level variation measurements required for fluids. In particular, using the U-type tube structure, the fluid is exposed to a pressure differential that causes the fluid to move through the U-tube at a first shear rate. This movement of fluid causes the pressure differential to decrease, thereby subjecting the movement of the fluid to a plurality of shear rates, i.e., decreasing shear rates from the first shear rate.

However, the governing equation and apparatus for the ER/MR-property measurement system are quite different from the scanning-capillary-tube viscometer. Thus, the present invention is a combination of the scanning-capillary-tube viscometer with an ER/MR-property measurement system.

Conventional rheometers utilize moving parts that must be calibrated, tend to wear and eventually must be replaced (e.g., pressure transducers). In addition, many of these rheometers must have test runs repeated in order to cover a range of shear rates, thereby making their use not only cumbersome but expensive.

Therefore, there remains a need for a rheometer that can measure the viscosity over range of shear rates, as well as the yield stress in an absolute zero shear rate range, of ER and MR fluids and which uses no moving parts, including pressure transducers. Furthermore, this rheometer must be simple to use, exhibit quick operation and be comparatively inexpensive.

SUMMARY OF THE INVENTION

An apparatus for determining the viscosity of a fluid (e.g., an electrorheological fluid, a magnetorheological fluid, etc.) over plural shear rates using a decreasing pressure differential. The apparatus comprises: a fluid source elevated at a first reference position above a horizontal reference position; a flow restrictor (e.g., a slit or capillary tube) having a first end and a second end and wherein the first end is in fluid communication with the fluid source and wherein the flow restrictor has some known dimensions; a lumen (e.g., a transfer tube) having one end in fluid communication with the second end of the flow restrictor and another end that is exposed to atmospheric pressure and wherein the lumen has a portion (e.g., a riser tube) that is positioned at an angle greater than zero degrees with respect to the horizontal reference position, and wherein a pressure differential exists between a column of fluid in the portion and the elevated fluid source; and whereby the column of fluid moves through the flow restrictor and the lumen at a first shear rate caused by the pressure differential; and whereby the movement of fluid causes the pressure differential to decrease from the first shear rate for generating the plural shear rates; a sensor (e.g., a light array/charge coupled device) for detecting the movement of the column of fluid and wherein the sensor generates data relating to the movement of the column of fluid over time; an electric/magnetic field generator for subjecting said flow restrictor to an electric/magnetic field (e.g., a static electric field, an alternating electric field, a static magnetic field, or an alternating magnetic field, etc.) when the fluid is flowing therein; and a processor, coupled to the sensor, for calculating the viscosity of the fluid over a range of plural shear rates based on the data relating to the movement of the column of fluid over time and the some known dimensions.

In accordance with another aspect of the invention, another apparatus is provided for determining the viscosity of a fluid (e.g., an electrorheological fluid, a magnetorheological fluid, etc.) over plural shear rates using a decreasing pressure differential. The apparatus comprises: a fluid source elevated at a first reference position above a horizontal reference position; a valve in fluid communication with the fluid source via a first port for controlling a flow of fluid from the fluid source; a flow restrictor (e.g., a slit or capillary tube) having a first end and a second end wherein the first end is in fluid communication with a second port of the valve and wherein the flow restrictor has some known dimensions and is positioned at the horizontal reference position; a lumen (e.g., a riser tube) having one end in fluid communication with a third port of the valve and another end that is exposed to atmospheric pressure and wherein the lumen is positioned at an angle greater than zero degrees with respect to the horizontal reference position; a processor coupled to the valve for controlling the valve to permit the flow of fluid into the lumen to form a column of fluid therein whereby a pressure differential is formed between a level of the column of fluid and the flow restrictor; the processor is also arranged for operating the valve to isolate the lumen from the fluid source and for coupling the flow restrictor and the lumen together to generate a falling column of fluid in the lumen; and whereby the falling column of fluid moves through the lumen, through the valve and the flow restrictor at a first shear rate caused by the pressure differential and wherein the movement of fluid causes the pressure differential to decrease from the first shear rate for generating the plural shear rates; a sensor (e.g., a light array/charge coupled device) for detecting the movement of the falling column of fluid and wherein the sensor generates data relating to the movement of the falling column of fluid over time; an electric/magnetic field generator for subjecting the flow restrictor to an electric/magnetic field (e.g., a static electric field, an alternating electric field, a static magnetic field or an alternating magnetic field, etc.) when the fluid is flowing therein; and wherein the processor, also coupled to the sensor, calculates the viscosity of the fluid over a range of plural shear rates based on the data relating to the movement of the falling column of fluid over time and the some known dimensions.

In accordance with another aspect of this invention, another apparatus is provided for determining the viscosity of a fluid (e.g., an electrorheological fluid, a magnetorheological fluid, etc.) over plural shear rates using a decreasing pressure differential. The apparatus comprises: a fluid source elevated at a first reference position above a horizontal reference position; a valve in fluid communication with the fluid source via a first port for controlling a flow of fluid from the fluid source, wherein the valve comprises a second port having a first lumen (e.g., a transfer tube) coupled thereto, and wherein the first lumen has a portion positioned at the horizontal reference position; a flow restrictor (e.g., a slit or capillary tube) having a first end and a second end, wherein the first end is in fluid communication with a third port of the valve and wherein the flow restrictor has some known dimensions; a second lumen (e.g., a riser tube) having one end in fluid communication with a said second end of the flow restrictor and another end that is exposed to atmospheric pressure, wherein the second lumen is positioned at an angle greater than zero degrees with respect to the horizontal reference position, and wherein the flow restrictor and the valve are located at a position below the horizontal reference position; a processor coupled to the valve for controlling the valve to permit the flow of fluid into the flow restrictor and the second lumen to form a column of fluid therein whereby a pressure differential is formed between a level of the column of fluid and the portion of the first lumen, wherein the processor is also arranged for operating the valve to isolate the flow restrictor and the second lumen from the fluid source and for coupling the flow restrictor and the second lumen to the first lumen to generate a falling column of fluid in the second lumen and the flow restrictor, wherein the falling column of fluid moving through the second lumen, through the flow restrictor, through the valve and through the first lumen at a first shear rate caused by the pressure differential, and wherein the movement of fluid causes the pressure differential to decrease from the first shear rate for generating the plural shear rates; a sensor (e.g., a light array/charge coupled device) for detecting the movement of the falling column of fluid, wherein the sensor generates data relating to the movement of the falling column of fluid over time; an electric/magnetic field generator for subjecting the flow restrictor to an electric/magnetic field (e.g., a static electric field, an alternating electric field, a static magnetic field, or an alternating magnetic field) when the fluid is flowing therein; and the processor, also coupled to the sensor, for calculating the viscosity of the fluid over a range of plural shear rates based on the data relating to the movement of the falling column of fluid over time and the some known dimensions.

In accordance with another aspect of this invention, another apparatus is provided for determining the viscosity of a fluid (e.g., an electrorheological fluid, a magnetorheological fluid, etc.) over plural shear rates using a decreasing pressure differential. The apparatus comprises: a fluid source elevated at a first reference position above a horizontal reference position; a valve in fluid communication with the fluid source via a first port for controlling a flow of fluid from the fluid source and wherein the valve further comprises a second port that is exposed to atmospheric pressure; a flow restrictor (e.g., a slit or capillary tube) having a first end, said flow restrictor having some known dimensions and being positioned at said horizontal reference position; a lumen (e.g., a riser tube) having one end in fluid communication with a third port of the valve and another end that is in fluid communication with the first end of the flow restrictor wherein the lumen is positioned at an angle greater than zero degrees with respect to the horizontal reference position; a processor coupled to the valve for controlling the valve to permit the flow of fluid into the lumen to form a column of fluid therein whereby a pressure differential is formed between a level of the column of fluid and the flow restrictor; the processor is also arranged for operating the valve to isolate the lumen from the fluid source and for coupling the lumen to the third port to generate a falling column of fluid in the lumen, wherein the falling column of fluid moves through the lumen and through the flow restrictor at a first shear rate caused by the pressure differential, and wherein the movement of fluid causes the pressure differential to decrease from the first shear rate for generating the plural shear rates; a sensor (e.g., a light array/charge coupled device) for detecting the movement of the falling column of fluid and wherein the sensor generates data relating to the movement of the falling column of fluid over time; an electric/magnetic field generator for subjecting said flow restrictor to an electric/magnetic field (e.g., a static electric field, an alternating electric field, a static magnetic field, or an alternating magnetic field) when the fluid is flowing therein; and the processor, also coupled to the sensor, for calculating the viscosity of the fluid over a range of plural shear rates based on the data relating to the movement of the falling column of fluid over time and the some known dimensions.

In accordance with another aspect of this invention, a method is set forth for determining the viscosity of a fluid (e.g., an electrorheological fluid, a magnetorheological fluid, etc.) over plural shear rates using a decreasing pressure differential. The method comprises the steps of: (a) elevating a fluid source above a horizontal reference position to establish a pressure differential between the fluid source and the horizontal reference position; (b) placing one end of a flow restrictor (e.g., a slit or capillary) in fluid communication with the fluid source and wherein the flow restrictor comprises some known parameters; (c) placing a second end of the flow restrictor in fluid communication with one end of a lumen (e.g., a riser tube) and wherein a second end of the lumen is exposed to atmospheric pressure; (d) positioning the lumen at angle greater than zero degrees with respect to the horizontal reference position;(e) allowing the fluid to flow from the fluid source through the flow restrictor and the lumen, thereby decreasing the pressure differential which causes the fluid to experience a plurality of shear rates; (f) applying an electric/magnetic field (e.g., a static electric field, an alternating electric field, a static magnetic field, or an alternating magnetic field) to the flow restrictor as the fluid flows through the flow restrictor (g) detecting the movement of the fluid through the lumen over time to generate data relating to the movement of the fluid through the lumen; and (h) calculating the viscosity of the fluid over a range of shear rates based on the data and the some known parameters.

In accordance with another aspect of this invention, another method is set forth for determining the viscosity of a fluid (e.g., an electrorheological fluid, a magnetorheological fluid, etc.) over plural shear rates using a decreasing pressure differential. The method comprises the steps of: (a) elevating a fluid source above a horizontal reference position and disposing the fluid source in fluid communication with a first port of a valve; (b) disposing one end of a lumen (e.g., a riser tube) in fluid communication with a second port of said valve with the other end of said lumen exposed to atmospheric pressure, said lumen being positioned at an angle greater than zero degrees; (c) disposing one end of a flow restrictor (e.g., a slit or capillary tube) in fluid communication with a third port of the valve at the horizontal reference position and wherein the flow restrictor comprises some known parameters; (d) operating the valve to couple the first port with the second port to generate a column of fluid of a predetermined length in the lumen, and wherein the column of fluid of predetermined length establishes a pressure differential between the column of fluid and the horizontal reference position; (e) operating the valve to decouple the second port from the first port and to couple the second port with the third port to generate a falling column of fluid in the lumen, thereby decreasing the pressure differential which causes the fluid to experience a plurality of shear rates; (f) applying an electric/magnetic field (e.g., a static electric field, an alternating electric field, a static magnetic field, or an alternating magnetic field) to the flow restrictor as the fluid flows through the flow restrictor; (g) detecting the movement of the fluid through the lumen over time to generate data relating to the movement of the fluid through the lumen; and (h) calculating the viscosity of the fluid over a range of shear rates based on the data and the some known parameters.

In accordance with another aspect of this invention, another method is set forth for determining the viscosity of a fluid (e.g., an electrorheological fluid, a magnetorheological fluid, etc.) over plural shear rates using a decreasing pressure differential. The method comprises the steps of: (a) elevating a fluid source above a horizontal reference position and disposing the fluid source in fluid communication with a first port of a valve; (b) disposing one end of a flow restrictor (e.g., a slit or capillary tube), having some known parameters, in fluid communication with a second port of the valve with the other end of the flow restrictor being in fluid communication with one end of a first lumen (e.g., a riser tube) and wherein the first lumen has another end exposed to atmospheric pressure, and wherein the first lumen is positioned at an angle greater than zero degrees with respect to the horizontal reference position; (c) positioning the flow restrictor and the valve below the horizontal reference position and coupling a third port of the valve with a second lumen (e.g., transfer tube) and wherein a portion of the second lumen is disposed at the horizontal reference position; (d) operating the valve to couple the first port with the second port to generate a column of fluid of a predetermined length in the flow restrictor and the first lumen and wherein the column of fluid of a predetermined length establishes a pressure differential between the column of fluid and the horizontal reference position; (e) operating the valve to decouple the second port from the first port and to couple the second port with the third port to generate a falling column of fluid in the flow restrictor and the first lumen, thereby decreasing the pressure differential which causes the fluid to experience a plurality of shear rates; (f) applying an electric/magnetic field (e.g., a static electric field, an alternating electric field, a static magnetic field, or an alternating magnetic field) to the flow restrictor as the fluid flows through the flow restrictor; (g) detecting the movement of the fluid through the the first lumen over time to generate data relating to the movement of the fluid through said first lumen; and (h) calculating the viscosity of the fluid over a range of shear rates based on the data and the some known parameters.

In accordance with another aspect of this invention, another method is set forth for determining the viscosity of a fluid (e.g., an electrorheological fluid, a magnetorheological fluid, etc.) over plural shear rates using a decreasing pressure differential. The method comprises the steps of: (a) elevating a fluid source above a horizontal reference position to establish a pressure differential between the fluid source and the horizontal reference position, and disposing the fluid source in fluid communication with a first port of a valve; (b) disposing one end of a lumen (e.g., a riser tube) in fluid communication with a second port of the valve with the other end of said lumen being in fluid communication with a flow restrictor (e.g., a slit or capillary tube) disposed at the horizontal reference position and wherein the flow resistor comprises some known parameters and wherein the lumen is positioned at an angle greater than zero degrees with respect to the horizontal reference position; (c) positioning a third port of the valve to be exposed to atmospheric pressure; (d) operating the valve to couple the first port with the second port to generate a column of fluid of a predetermined length in the lumen; (e) operating the valve to decouple the second port from the first port and to couple the second port with the third port to generate a falling column of fluid in the lumen, thereby decreasing the pressure differential which causes the fluid to experience a plurality of shear rates; (f) applying an electric/magnetic field (e.g., a static electric field, an alternating electric field, a static magnetic field, or an alternating magnetic field) to the flow restrictor as the fluid flows through the flow restrictor; (g) detecting the movement of the fluid through the lumen over time to generate data relating to the movement of the fluid through the lumen; and (h) calculating the viscosity of the fluid over a range of shear rates based on the data and the some known parameters.

DESCRIPTION OF THE DRAWINGS

FIG. 2A is an enlarged isometric view of the slit used for applying a static/alternating electric field to an ER fluid passing therethrough and for applying a static/alternating magnetic field to an MR fluid passing therethrough, respectively;

FIG. 2B is a Cartesian coordinate system as it applies to the slit;

FIG. 2C is an enlarged isometric view of the slit used for passing an MR fluid and which is subjected to a static/alternating magnetic field having north and south poles that form the wall of the slit;

FIG. 2D is an enlarged isometric view of the capillary tube for passing an MR fluid and which is subjected to a static/alternating magnetic field from an adjacent magnetic field applicator;

FIGS. 13C–13D depict the valve mechanism operation during the test run of the first embodiment;

DETAILED DESCRIPTION OF THE PREFERRED EMBODIMENTS

Figure 1:
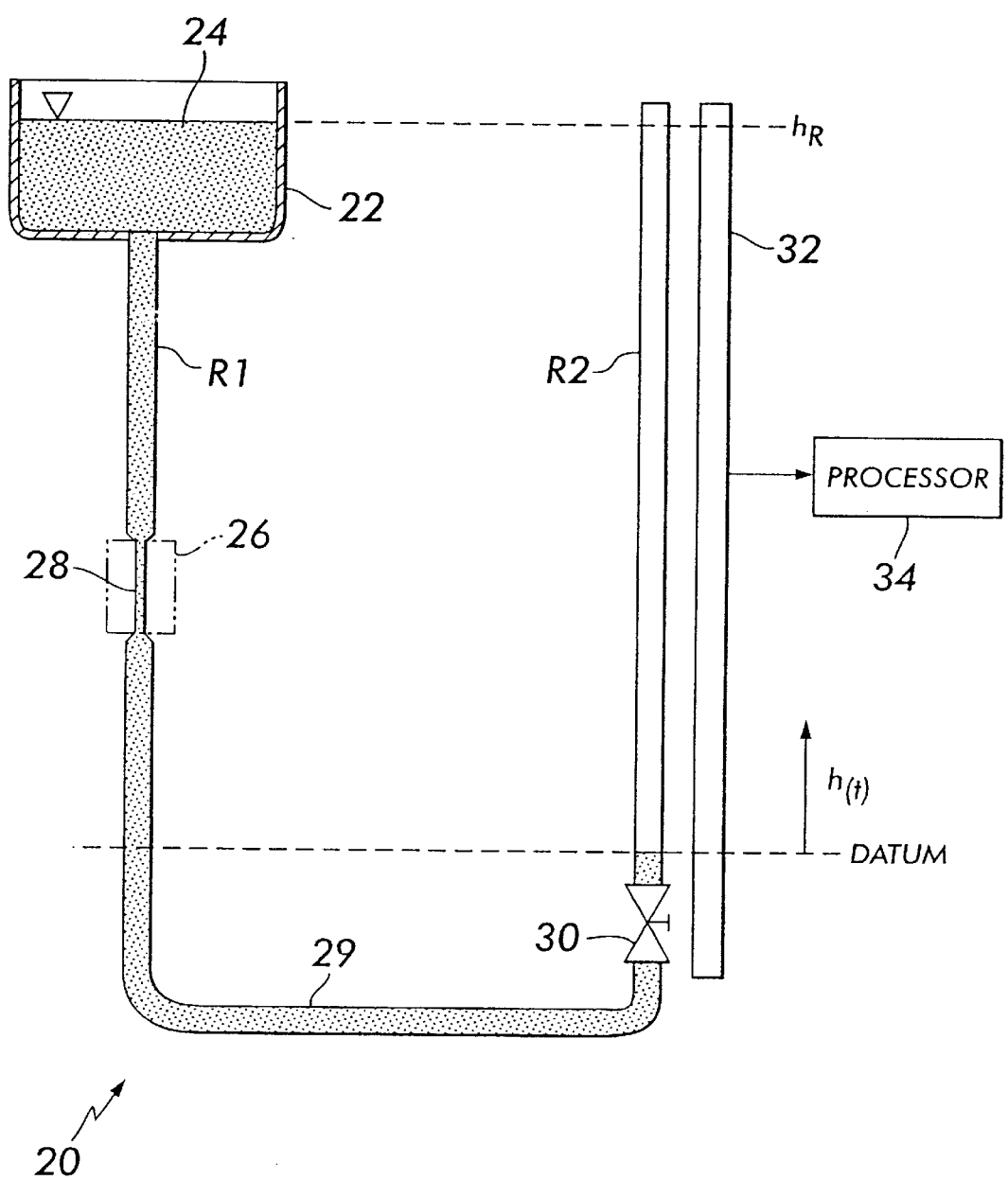
FIG. 1 is a block diagram of the ER/MR fluid scanning rheometer apparatus.

Referring now in detail to the various figures of the drawing wherein like reference characters refer to like parts, there is shown at 20 an ER/MR fluid scanning rheometer.

In particular, the rheometer 20 comprises a constant-fluid level, overhead tank or reservoir 22 containing the ER fluid or the MR fluid 24. This tank 22 is coupled to a riser tube R1. An electric/magnetic field generator 26 imposes an electric field, or a magnetic field, or both (depending on what type of fluid 24 is being analyzed) on a flow restrictor 28 of the riser tube R1 that comprises either a slit or a capillary tube; suffice it to say for now that where the fluid 24 is an ER fluid that is being analyzed using the rheometer 20, the restrictor 28 comprises a slit whereas if the fluid 24 being analyzed is an MR fluid, either a slit or a capillary tube is used for the restrictor 28. A transfer tube 29 couples the riser tube R1 to a valve 30 (e.g., on/off) which is used to control the flow of the fluid 24. A column level detector 32 is used is to monitor the movement of the fluid 24 as it rises up through a second riser tube R2, that is vented to atmosphere. A processor 34 is coupled to the column level detector 32 (e.g., a video camera, a light array/CCD described below, etc.) for analyzing the height vs. time data (h(t)) from the column level detector 34, along with the slit/capillary data, to determine the fluid viscosity and yield stress. The height of the fluid 24 column in R2 (h(t)) is determined from a datum level and the constant level of the fluid 24 in the overhead reservoir 22 is known as $h_R$. It should be noted that the riser tube R2 can be positioned at any angle greater than zero degrees with respect to the horizontal reference position, e.g., datum level; in FIG. 1 this angle is 90°.

In the preferred embodiment, the riser tube R1, flow restrictor 28, transfer tube 29 and riser tube R2 form a "U"-tube structure that is in an upright position; except for the generator 26, this structure is similar to the structure disclosed in application Ser. No. 09/439,795 (now U.S. Pat. No. 6,322,524 (Kensey et al.)) and application Ser. No. 09/573,267 (now U.S. Pat. No. 6,402,703 (Kensey et al.)), both entitled DUAL RISER/SINGLE CAPILLARY VISCOMETER, both of which are assigned to the same Assignee, namely Rheologics, Inc. (formerly Visco Technologies, Inc.) of the present invention and both of whose entire disclosures are incorporated by reference herein. Using this configuration, the test fluid 24 is subjected to a decreasing pressure differential that moves the test fluid 24 through a plurality of shear rates (i.e., from a high shear rate at the beginning of the test run to a low shear rate at the end of the test run), which is especially important in determining the viscosity of non-Newtonian fluids, as set forth in application Ser. No. 09/439,795 (now U.S. Pat. No. 6,322,524 (Kensey et at.)) and application Ser. No. 09/573,267 (now U.S. Pat. No. 6,402,703 (Kensey et al.)). In particular, because of the elevated position of the reservoir 22 and with the second riser R2 exposed to atmospheric pressure, when the valve 30 is opened, the test fluid 24 flows through the riser tube R1, flow restrictor 28, transfer tube 29 and up the riser tube R2. A pressure differential exists between the column of fluid in the riser tube R2 and the elevated reservoir 22. As the test fluid 24 flows up the riser tube R2, the movement of the test fluid 24 causes the pressure differential to decrease, thereby causing the test fluid 24 to slow down. This movement of the test fluid 24, initially at a high shear rate and diminishing to a slower shear rate, thus covers a plurality of shear rates. However, it should be understood that it is within the broadest scope of this invention to include any other configurations where the test fluid 24 can be subjected to a decreasing pressure differential in order to move the test fluid through a plurality of shear rates.

It should be understood that the term "electric/magnetic field" as used throughout this Specification implies an electric field, a magnetic field or both an electric field and a magnetic field together. Similarly, the term "electric/magnetic field generator" as used throughout this Specification implies a generator capable of generating an electric field, a magnetic field or both an electric field and a magnetic field together. Furthermore, as will be discussed in detail below, the term "electric/magnetic field" also implies that where an electric field is applied, the electric field may be either static or alternating, or where a magnetic field is applied, the magnetic field may be either static or alternating; where an electric field is applied simultaneously with a magnetic field, alternating electric and magnetic fields are implied.

Figure 2E:
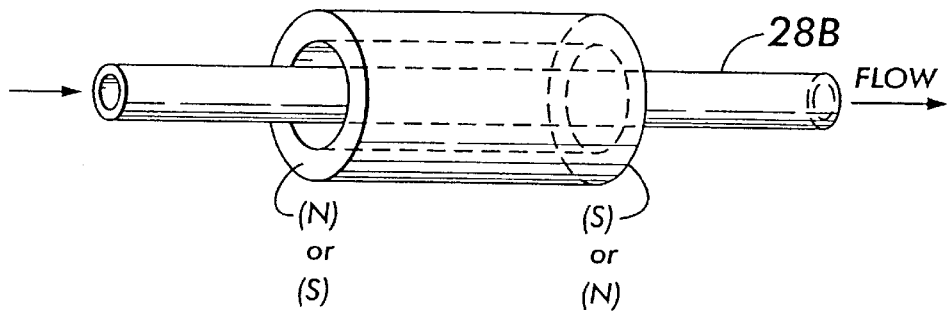
FIG. 2E depicts alternative means of generating the magnetic field around the capillary tube that is carrying an MR fluid.
Figure 2F:
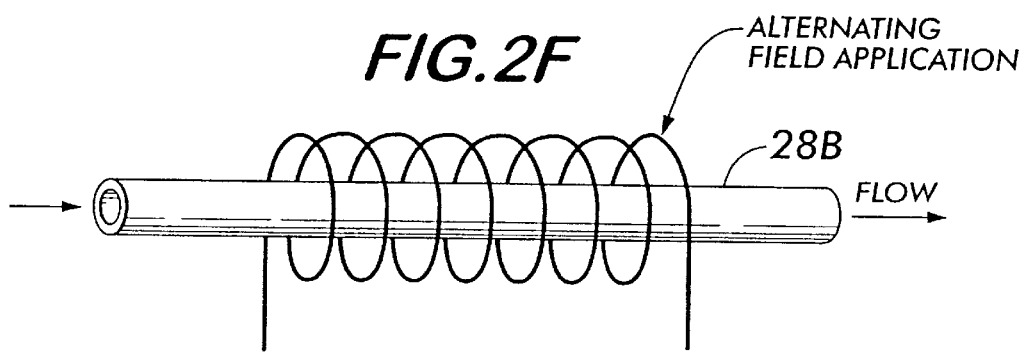
FIGS. 2F–2G depicts alternative means of generating an alternating electric/magnetic field around the capillary tube.
Figure 2G:
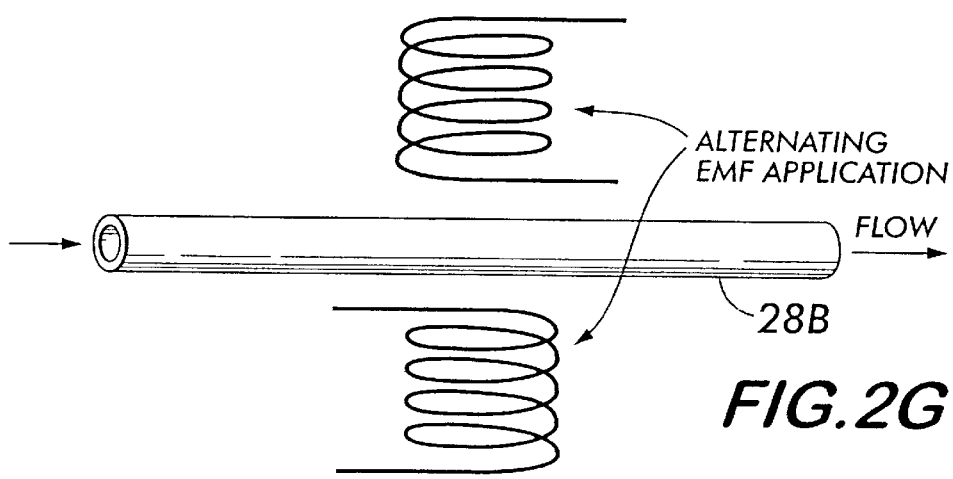

As mentioned earlier, the flow restrictor 28 of R1 may comprise either a slit 28A or a capillary tube 28B. FIGS. 2A–2C depict enlarged views of these configurations. In particular, FIGS. 2A–2B depict the slit comprising a pair of walls 36A and 36B, whose inner surfaces 38A/38B are in direct contact with the fluid 24 during flow; in contrast, as shown in FIG. 2C, a capillary tube 28B is used to confine the flow of MR fluid therein, with the walls 36A and 36B being adjacent the capillary tube 28B. The use of a slit 28A is necessary for subjecting ER fluids to a static/alternating electric field, i.e., because air is an insulator to electric current, it is necessary to have the ER fluid 24 make contact with the walls 36A/36B; however, since magnetic fields are capable of passing through air, direct contact with the MR fluid is unnecessary and thus either the slit 28A (FIG. 2B) or the capillary tube 28B (FIG. 2C) can be used for restrictor 28 for generating the north (N)-south (S) pole configuration. The electric field generator 26 may comprise any conventional DC voltage supply that can generate electric fields in the 10 kV/mm range; it should be understood that the electric field generator may also comprise any AC voltage supply where both the magnitude and frequency can be varied depending on the ER fluid under test. The magnetic field generator 26 may comprise any conventional magnetic field generators for generating magnetic fields in the range of 100–1000 Gauss range, including any of the configurations shown in FIGS. 2D–2G; these coil configurations may be coupled to a function generator and amplifier that can generate an alternating electric/magnetic field where both the magnitude and frequency can be varied.

Figure 8:
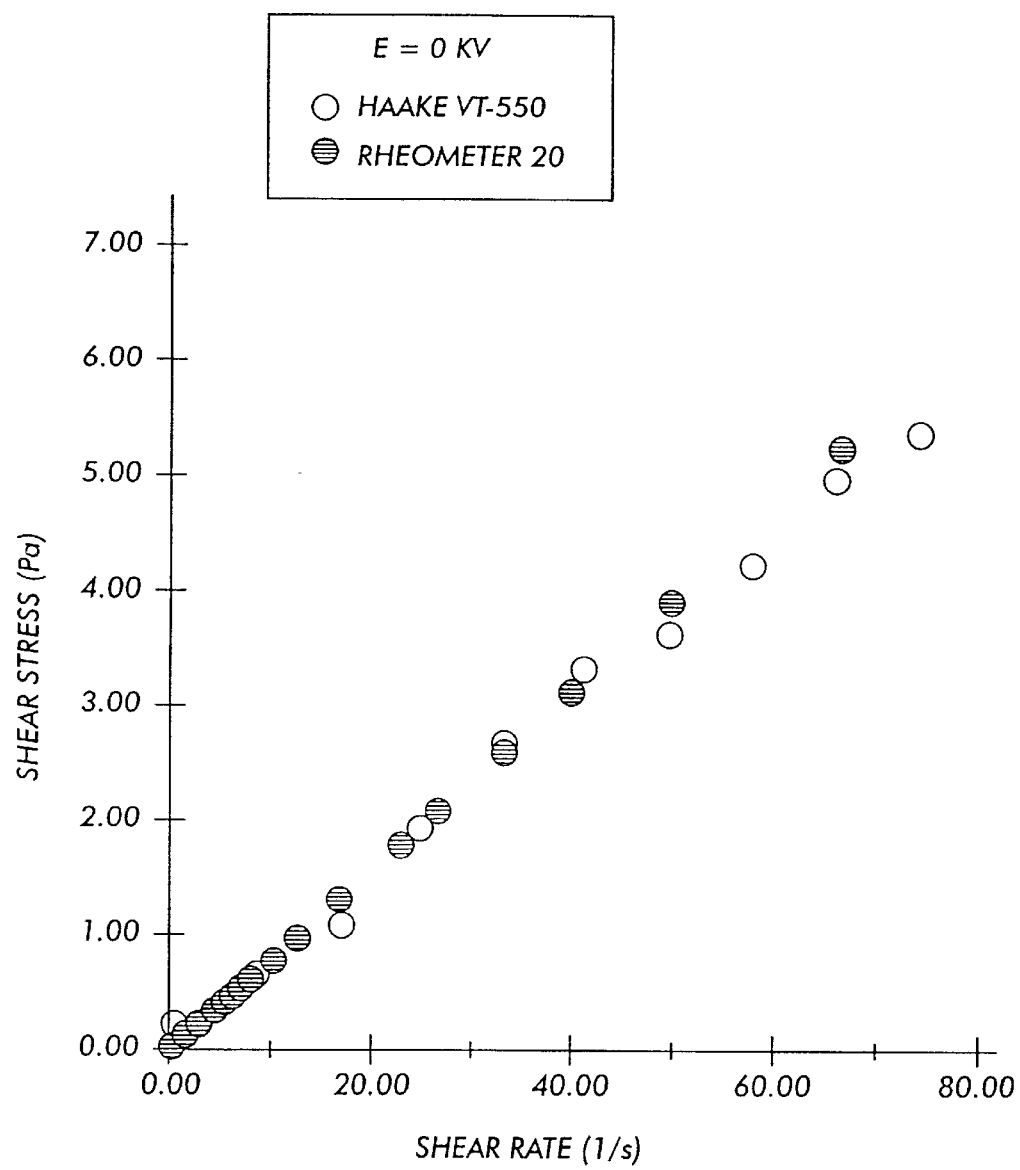
FIG. 8 is a shear stress vs. shear rate curve of the first test ER fluid as determined by the present invention and by a conventional rotating viscometer (e.g., Haake VT-550)
Figure 10:
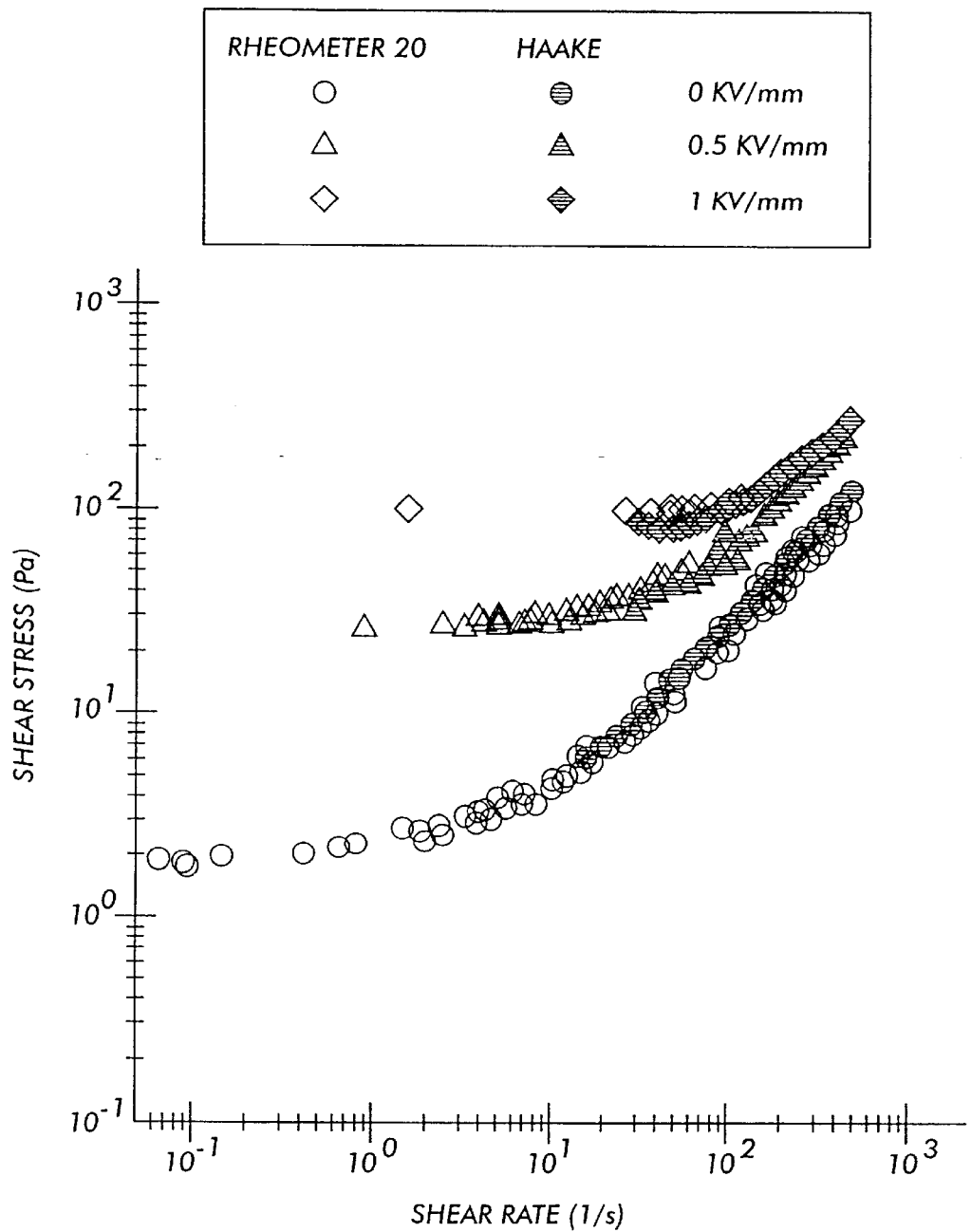
FIG. 10 are shear stress vs. shear rate curves of the second test ER fluid using static electric fields of 0 kV/mm, 0.5 kV/mm and 1 kV/mm.

Using the rheometer 20 described above, two exemplary ER fluids were analyzed for viscosity and yield stress and the results were compared with a conventional rotating-type viscometer, i.e., Haake VT-550 (FIGS. 8 and 10). The first ER fluid comprised a zeolite-corn oil mixture (40:60 by weight); in selecting various test suspensions, the zeolite and corn oil were chosen as dispersed particles and suspending medium, respectively. The mean diameters of the zeolite particles ranged from 5 μm to 30 μm. The volume concentration was fixed at 40% for the test. No surfactant was added in the test suspension. The second ER fluid comprised a cornstarch-corn oil mixture (15:85 by weight).

The rheometer 20 comprised the following during the test run: the slit gap ($G_S$) and the longitudinal length ($L_S$) were 1.3 mm and 200 mm, respectively; the slit width ($W_S$) was 30 mm. The inside diameters of the transfer tube 29 and riser tubes R1/R2 were 6 and 6.5 mm, respectively. The lengths of the transfer tube 29 and riser tubes R1/R2 were 200 mm and 800 mm, respectively. The inside diameter and length of the transfer tube 29 and riser tubes R1/R2 were chosen to ensure that the pressure drops in the tubes were significantly smaller than that in the slit 28A; for example the diameter of the transfer tube 29 was 6 mm and the diameter of the riser tube R2 was 6.5 mm. The riser tubes R1/R2 comprised glass tubes, the valve mechanism 30 was an on/off valve, the column level detector 32 comprised a video camera, and the processor 34 was a computer data acquisition system. The value for $h_R$ from the datum was 1525 mm.

At the beginning of the test, with the on/off valve 30 closed, the ER fluid 24 was filled in the overhead reservoir 22, the slit 28A, and the transfer tube 29. Next, the fluid level in the reservoir 22 was measured. At this time, a DC voltage was applied across the slit 28A. Then, the on/off valve 30 was opened, and the ER fluid 24 began filling the riser tube R2. The walls 36A/36B of the slit 28A comprised two copper plates (30 mm×200 mm), to which the DC voltage was applied. The column level detector 32 (e.g., a video camera) was used for measuring the fluid level by recording the fluid level with respect to time, h(t), in the riser tube R2. In order to minimize the reading error, the video camera 32 was linearly traversed along a linear guide (not shown) as the fluid level rose. The recorded images were magnified, and the fluid level was read using an image treatment tool (e.g., Paint Shop Pro™) to minimize reading errors. One could determine the actual height change in the rising tube with an accuracy of 0.2 mm.

As the fluid level in the riser tube R2 increased, the head difference between the reservoir 22 and the level of the ER fluid in riser tube R2 continued to decrease. Accordingly, the rising speed of the fluid level in the riser tube R2 gradually decreased as the fluid level in the riser tube R2 approached that of the reservoir 22, and the ER fluid eventually stopped rising. It took approximately five to ten minutes for the fluid level in the riser tube R2 to reach a plateau value for the ER fluid. The time to complete a run varied depending on types of liquids and the applied electric field strength.

In order to determine the Theological property of the ER fluid using the present system, it is necessary to know the pressure drop across the slit ($\Delta P_{SL}$). However, what was measured in the present system was the total pressure drop across the entire system ($\Delta P_{total}$). In other words, the total head difference between the reservoir 22 and the column level in the riser tube R2, $h_R-h(t)$, includes not only the pressure drop across the slit 28A ($\Delta P_{SL}$), but also the pressure drop across the transfer tube 29 ($\Delta P_{transfer}$) and the riser tubes R1/R2 ($\Delta P_{riser}$) If a quasi-steady state is assumed during the test, the pressure drop across each tube (R1, 29 and R2) can be estimated based on the laminar flow theory of an incompressible fluid. Thus, the pressure drops occurring in both the transfer tube 29 and the riser tubes R1/R2 should be subtracted from the total pressure drop. The pressure drop across the slit 28A ($\Delta P_{SL}$) can be described as:

$$\Delta P_{SL} = \Delta P_{total} - (\Delta P_{transfer} + \Delta P_{riser}) \quad (3)$$

$$\Delta P_{total} = \rho g (h_R - h(t)) \quad (4)$$

where $h_R$ is the constant fluid level in the overhead reservoir 22 and h(t) is an instantaneous fluid level in the riser tube R2; ρ is the density of the ER fluid and "g" is the gravitational constant. It should be noted that the contribution from the second term on the right hand side in Eq. (1) is less than 0.5%. Hence the term can be neglected for all practical purpose.

The fluid level in the riser tube R2 is the only quantity to be measured. It should be noted that the height vs. time curve (FIG. 4) provides the data not only for the total head pressure ($\Delta P_{total}$) but also for the fluid velocity ($V_{riser}$) in the riser tube R2. This fluid velocity, $V_{riser}$, can be calculated from the gradient of the fluid level curve, h(t), as follows:

$$V_{riser} = \frac{dh(t)}{dt} \quad (5)$$

From the fluid velocity in the riser tube R2, the velocity at the slit 28A ($V_{SL}$) and volume flow rate are determined as shown below:

$$V_{SL} = \frac{dh(t)}{dt} \frac{A_{riser}}{A_{SL}} \quad (6)$$

$$Q = A_{SL} V_{SL} = \frac{dh(t)}{dt} A_{riser} \quad (7)$$

where "A" represents the area of the indicated components.

Figure 3A:
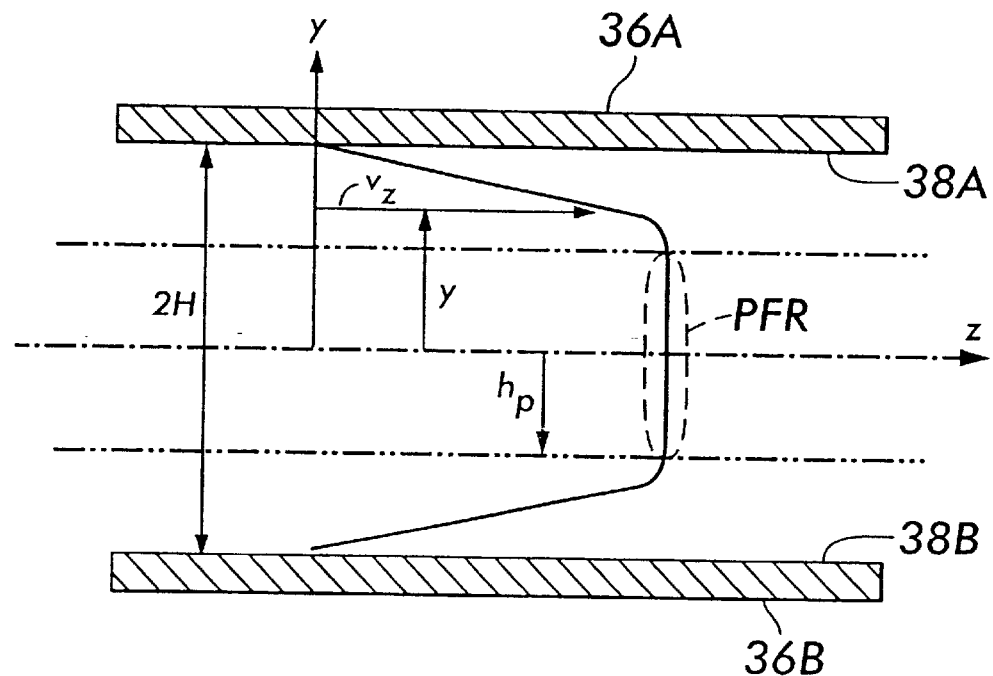
FIG. 3A is a velocity profile of an ER fluid taken along line 3A–3A of FIG. 2A.
Figure 3B:
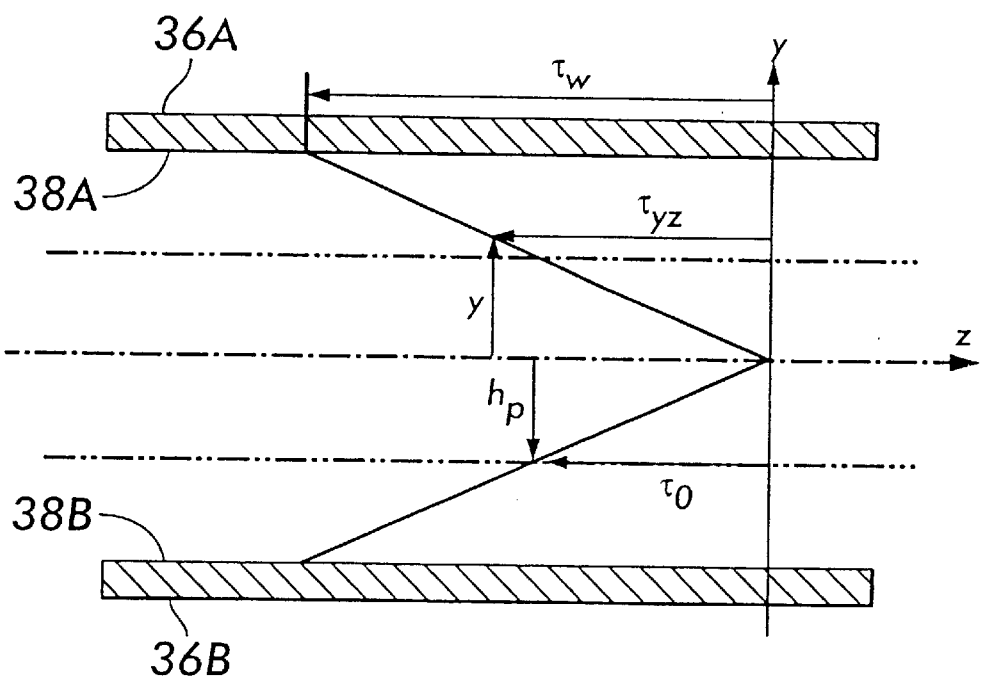
FIG. 3B is a shear stress profile an ER fluid taken along 3A–3A of FIG. 2A.

In determining the Herschel-Bulkley parameters, certain assumptions were made; FIG. 2B depicts the Cartesian coordinates referenced below; FIG. 3A depicts the flow velocity profile; and FIG. 3B depicts the shear stress profile of the flow. The assumptions made during the test were:

1) a fully-developed, steady, isothermal, laminar flow;
2) no velocity in the x and y directions (see FIG. 2A);
3) no slip at the walls 36A/36B, $V_z=0$ at y=±H, and;
4) the fluid is incompressible with viscosity being independent of pressure.

In order to determine the shear stress of the ER fluid, the pressure drop across the entire system is necessary. In the test, the wall shear stress, $\tau_w$, can be expressed with the pressure drop as follows:

$$\tau_w(t) = \frac{\Delta P_{SL} H}{L \left(1 + \frac{2H}{W}\right)} \quad (8)$$

where H is the half of the slit gap ($G_S$), L is the slit length ($L_S$), W is the slit width ($W_S$)

It should be noted that ER fluids under the influence of a static/alternating electric field apparently exhibit yield stresses. In this test, the yield stress at a low (e.g., zero) shear rate can be determined from Equation (8) at the final hydrostatic equilibrium state. In other words, the yield stress of an ER fluid causes a fluid level difference between the level of the overhead reservoir 22 and the column level in the riser tube R2 even at t=∞.

$$\tau_0 = \frac{\Delta P_{SL}(t=\infty)H}{L\left(1+\frac{2H}{W}\right)} \quad (9)$$

where $\Delta P_{SL}$ (t=∞) represents the pressure difference across the slit 28A at the final equilibrium state.

Meanwhile, the shear rate information for the Herschel-Bulkley fluid flowing in the slit 28A is obtained from experimental data with a suitable mathematical treatment. For Bingham plastic or power-law fluids, the shear rates were determined from the flow rate and pressure drop quantities and can be obtained from any standard handbook. (e.g., R. B. Bird, R. C. Amstrong and O. Hassager, "Dynamics of Polymeric Liquids", Vol. 1, *Fluid Mechanics*, Wiley 1987). For a Herschel-Bulkley fluid, it is necessary to derive equations with a similar procedure for Bingham plastic and power-law fluids.

In the test, only a longitudinal shear flow was considered, hence there is only one non-zero velocity component. Also, the aspect ratio of the slit 28A is 1:23 so that the flow can be assumed as one-dimensional flow; this velocity component is taken to be $V_Z(y)$ in the z-direction. Hence, the momentum flux distribution for flow of any kind of fluid through the slit 28A is given by the following equation:

$$\tau_{yz} = \left(\frac{\Delta P}{L}\right)y = \tau_0 + K\dot{\gamma}^n \quad (10)$$

Both distribution of velocity and shear stress for a Herschel-Bulkley fluid are shown in FIGS. 3A and 3B, respectively. Substituting the Herschel-Bulkley model, Equation 2 into Equation 10, then gives the following differential equation for the velocity:

$$\frac{dV_Z}{dy} = -\left(\frac{\Delta P}{KL}y - \frac{\tau_0}{K}\right)^{\frac{1}{n}} \quad (11)$$

The volume flow rate of the Herschel-Bulkley fluid flow in the slit 28A may be calculated from:

$$Q = 2W\int_0^H V_Z(y)dy \quad (12)$$

Integrating Equation 14 by parts and using the non-slip condition, the following is obtained:

$$Q = -2W\int\left(\frac{dV_Z}{dy}\right)ydy \quad (13)$$
$$= -2W\left[\int_0^{h_p}\left(\frac{dV_Z}{dy}\right)ydy + \int_{h_p}^H\left(\frac{dV_Z}{dy}\right)ydy\right]$$

where $h_p$ represents the distance from the centerline of the plug flow region, as shown in FIGS. 3A/3B; the plug flow region is defined as that region where velocity is constant, (see PFR, FIG. 3A) and is due to the presence of yield stress. The first integral in Equation 13 becomes zero because $dV_Z/dy=0$ for $y \leq h_p$, as shown in FIG. 3A. Hence, the volume flow rate of the flow is:

$$Q = -2W\left[\int_{h_p}^H\left(\frac{dV_Z}{dy}\right)ydy\right] \quad (14)$$

Now, the shear rate $dV_Z/dy$ is related with the volume flow rate, but it is in the integral. In order to obtain the shear rate, a mathematical treatment is required to replace the y-variable with τ. As shown in FIG. 3B, the shear stress profile can be described by the y-variable:

$$\tau = \frac{\tau_w}{H}y \quad (15)$$

From the above Equation 15 gives $dy=(H/\tau_w)d\tau$. Replacing the y-variable with τ using Equation 14 gives:

$$\frac{Q\tau_w^2}{2WH^2} = -\int_{\tau_0}^{\tau_w}\frac{dV_Z}{dy}\tau d\tau \quad (16)$$

Now, substituting Equation 11 of the Herschel-Bulkley model into Equation 18, integrating and then re-arranging, yields the following flow rate of the Herschel-Bulkley fluid:

$$Q = \frac{2WH^2}{2n+1}\left(\frac{\tau_w}{K}\right)^{\frac{1}{n}}\left(1-\frac{\tau_0}{\tau_w}\right)^{1+\frac{1}{n}}\left(1+\frac{n}{n+1}\frac{\tau_0}{\tau_w}\right) \quad (17)$$

Figure 4:
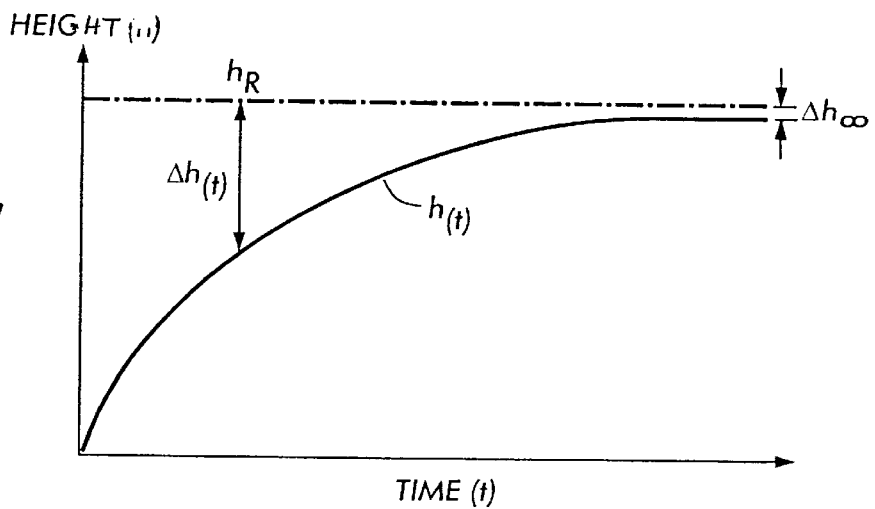
FIG. 4 is height vs. time plot based on the ER (or MR) fluid column level of the riser tube R2 in the rheometer apparatus.

From the above Equation 17, the flow consistency, K, can be determined. Also, re-arranging Equation 17 provides the shear rate, $\dot{\gamma}$, as follows:

$$\dot{\gamma}_w = \left(\frac{\tau_w-\tau_0}{K}\right)^{\frac{1}{n}} = \frac{Q}{2WH^2}\left(2+\frac{1}{n}\right)\left[(1-c)\left(1+\frac{n}{n+1}c\right)\right]^{-1} \quad (18)$$
$$= \frac{1}{3}\dot{\gamma}_{aw}\left(2+\frac{1}{n}\right)\left[(1-c)\left(1+\frac{n}{n+1}c\right)\right]^{-1}$$

where $\dot{\gamma}_{aw}$ is the apparent or Newtonian shear rate at the wall, $$\dot{\gamma}_{aw} = \frac{3Q}{2WH^2} = \frac{3A_{riser}}{2WH^2}\frac{dh(t)}{dt} \quad (19)$$

and c is the distance ratio of the plug flow region to the wall from the centerline which can be defined as follows:

$$c = \frac{h_p}{H} = \frac{\tau_0}{\tau_w} = \frac{\Delta h(t=\infty)}{\Delta h(t)} \quad (20)$$

where $\Delta h(t)$ and $\Delta h$ (t=∞), which is also referred to as $\Delta h_\infty$, are defined as shown in FIG. 4 and n is the power-law exponent which can be defined and determined as:

$$n = \frac{d\ln\Delta P}{d\ln Q} = \frac{d\ln\left(\frac{H\Delta h(t)-\Delta h_\infty}{L\left(1+\frac{2H}{W}\right)}\right)}{d\ln\left(\frac{dh(t)}{dt}A_r\right)}. \quad (21)$$

When c is zero, the shear rate for the Herschel-Bulkley model in Equation 18 reduces to that of the power-law model, $$\dot{\gamma}_w = \frac{1}{3}\dot{\gamma}_{aw}\left(2 + \frac{1}{n}\right).$$

Meanwhile, when n becomes 1, the shear rate for the Herschel-Bulkley model reduces to that of the Bingham plastic model, $$\dot{\gamma}_w = \frac{\dot{\gamma}_{aw}}{(1-c^2)}.$$

Thus, the shear rate can be determined from the shear stress at the same point (i.e., at the wall) in Equation 7. Therefore, the Herschel-Bulkley viscosity, $\eta_{HB} = K\dot{\gamma}_w^n$, can be directly related with the volume flow rate and pressure drop as follows:

$$\eta_{HB} = \frac{\tau_w - \tau_0}{\dot{\gamma}_w} = \frac{2\rho g 2WH^3}{L\left(1 + \frac{2H}{W}\right)A_{riser}} \frac{(1-c)\left(1 + \frac{n}{n+1}c\right)}{\left(2 + \frac{1}{n}\right)} \frac{\Delta h(t) - \Delta h_\infty}{\frac{dh(t)}{dt}} \quad (22)$$

Meanwhile, the generalized Newtonian viscosity ($\eta$) of the Herschel-Bulkley fluid corresponding to the wall shear rate can also be determined from the measured quantity, h(t) as:

$$\eta = \frac{\tau_w}{\dot{\gamma}_w} = \frac{2\rho g 2WH^3}{L\left(1 + \frac{2H}{W}\right)A_{riser}} \frac{(1-c)\left(1 + \frac{n}{n+1}c\right)}{\left(2 + \frac{1}{n}\right)} \frac{\Delta h(t)}{\frac{dh(t)}{dt}} \quad (23)$$

Furthermore, based on Equation 9, the yield stress $\tau_0$ is given by:

$$\tau_0 = \frac{\rho g \Delta h_\infty H}{L\left(1 + \frac{2H}{W}\right)} \quad (23A)$$

The above analysis is the same where a magnetorheological (MR fluid) is used along with the slit 28A. In contrast, where a magnetorheological (MR) fluid is used, and instead of the slit 28A, a capillary tube 28B is used, the equations for the viscosity and shear stress are slightly modified.

In particular, using the capillary tube 28B having a radius (R) and utilizing a cylindrical coordinate system, assumptions no. 2 and no. 3 (mentioned previously) are:

2) no velocity in the radial direction (r) and angular direction ($\theta$); and 3) no slip at the walls 36A/36B, $V_Z=0$ at r=R.

Furthermore, as with the ER fluids, since the fluid level in the riser tube R2 is the only quantity that needs to be measured, the fluid velocity in the riser tube R2 is also given by Equation (5). As a result, both the velocity and volume flow rate for the flow in the capillary tube 28B is given by Equations (6) and (7), respectively, but with $V_{SL}$ replaced with $V_C$ and $A_{SL}$ replaced with $A_C$. Thus, the expression for wall shear stress, $\tau_w$, is expressed as:

$$\tau_w(t) = \frac{\Delta P_C R}{2L} \quad (24)$$

where L is the length of the capillary tube 28B and $\Delta P_C$ represents the pressure drop across the capillary tube 28B. Similarly, the yield stress at low (zero) shear rate can be determined from Equation (7) at the final hydrostatic equilibrium state where the yield stress of an MR fluid causes a fluid level difference between the reservoir 22 fluid level and the riser tube R2 column level even at time t=∞ as:

$$\tau_0 = \frac{\Delta P_C(t=\infty)R}{2L} \quad (25)$$

where $\Delta P_C(t=\infty)$ represents the pressure difference across the capillary tube 28B at the final equilibrium state.

Meanwhile, the shear rate information for the Herschel-Bulkley fluid flowing in the capillary tube 28B is obtained from experimental data with a suitable mathematical treatment. For Bingham plastic or power-law fluids, the shear rates were determined from the flow rate and pressure drop quantities and can be obtained from any standard handbook. (e.g., R. B. Bird, R. C. Amstrong and O. Hassager, "Dynamics of Polymeric Liquids", Vol. 1, *Fluid Mechanics*, Wiley 1987). For a Herschel-Bulkley fluid, it is necessary to derive equations with a similar procedure for Bingham plastic and power-law fluids.

In the test, only a longitudinal shear flow was considered, hence there is only one non-zero velocity component. Adopting cylindrical coordinates, the velocity, $V_Z(r)$ is defined in the z-direction. Hence, the momentum flux distribution for flow of any kind of fluid through the capillary tube 28B is given by the following equation:

$$\tau_z = \left(\frac{\Delta P_C}{2L}\right)r = \tau_0 + K\dot{\gamma}^n \quad (26)$$

Both distribution of velocity and shear stress for a Herschel-Bulkley fluid are shown in FIGS. 3A and 3B, respectively, but with the term "y" replaced with the "r". Substituting the Herschel-Bulkley model, Equation 2 into Equation 10, then gives the following differential equation for the velocity:

$$\frac{dV_Z}{dr} = -\left(\frac{\Delta P}{2KL}r - \frac{\tau_0}{K}\right)^{\frac{1}{n}} \quad (27)$$

The volume flow rate of the Herschel-Bulkley fluid flow in the capillary tube 28B may be calculated from:

$$Q = 2\pi \int_0^R V_Z \dot{\gamma}(r) \quad (28)$$

Integrating Equation 28 by parts and using the non-slip condition, the following is obtained:

$$Q = 2\pi\left[\int_0^{r_0} V_Z r\, dr + \int_{r_0}^R V_Z r\, dr\right] \quad (29)$$

The first integral in Equation (29) becomes zero when $dV_Z/dr=0$ for $r \leq r_0$ where $r_0$ replaces $h_p$ in FIGS. 3A/3B which represents the radial distance from the centerline of the plug flow region. Hence, the volume flow rate of the flow is:

$$Q = -\pi\left[\int_{r_0}^R \left(\frac{dV_Z}{dr}\right)r^2\, dr\right] \quad (30)$$

Now, the shear rate $dV_Z/dr$ is related with the volume flow rate, but it is in the integral. In order to obtain the shear rate, a mathematical treatment is required to replace the r-variable with $\tau$. As shown in FIG. 3B, the shear stress profile can be described by the r-variable:

$$\tau = \frac{\tau_w}{R} r \qquad (31)$$

From the above Equation 31 gives $dr=(R/\tau_w)d\tau$. Replacing the r-variable with $\tau$ using Equation 27 gives:

$$\frac{Q\tau_w^3}{\pi R^3} = -\int_{\tau_0}^{\tau_w} \frac{dV_z}{dr} \tau^2 d\tau \qquad (32)$$

Now, substituting Equation 27 of the Herschel-Bulkley model into Equation 32, integrating and then re-arranging, yields the following flow rate of the Herschel-Bulkley fluid:

$$Q = \frac{2n\pi R^3}{n+1}\left(\frac{\tau_w}{K}\right)^{\frac{1}{n}}(1-c)^{1+\frac{1}{n}}\left(\frac{1}{2} - \frac{n}{2n+1}(1-c) + \frac{n^2(1-c)^2}{(2n+1)(3n+1)}\right) \qquad (33)$$

where $c = \dfrac{\tau_0}{\tau_w} = \dfrac{\Delta h_\infty}{\Delta h(t)}$ and where $$\beta = (1-c)^{1+\frac{1}{n}}\left(\frac{1}{2} - \frac{n}{2n+1}(1-c) + \frac{n^2(1-c)^2}{(2n+1)(3n+1)}\right)$$

From the above Equation 33, the flow consistency, K, can be determined. Also, re-arranging Equation 33 provides the shear rate, $\dot\gamma$, as follows:

$$\dot\gamma_w = \left(\frac{\tau_w - \tau_0}{K}\right)^{\frac{1}{n}} = \frac{1}{4}\left(\frac{4Q}{\pi R^3}\right)\left(1 + \frac{1}{n}\right)\frac{1}{\beta} \qquad (34)$$

$$= \frac{1}{4}\dot\gamma_{aw}\left(1 + \frac{1}{n}\right)\frac{1}{\beta}$$

where $\dot\gamma_{aw}$ is the apparent or Newtonian shear rate at the wall, $$\dot\gamma_w = \frac{4Q}{\pi R^3} = \frac{4 A_{riser}}{\pi R^3} \frac{dh(t)}{dt} \qquad (35)$$

and c is the distance ratio of the plug flow region to the wall from the centerline which can be defined as follows:

$$c = \frac{r_0}{R} = \frac{\tau_0}{\tau_w} = \frac{\Delta h(t = \infty)}{\Delta h(t)} \qquad (36)$$

and n is the power-law exponent which can be defined and determined as:

$$n = \frac{d\ln\Delta P}{d\ln Q} = \frac{d\ln\left(\frac{\rho g R(\Delta h(t) - \Delta h_\infty)}{2L}\right)}{d\ln\left(\frac{dh(t)}{dt} A_{riser}\right)} \qquad (37)$$

When c is zero, the shear rate for the Herschel-Bulkley model in Equation 34 reduces to that of the power-law model, $$\dot\gamma_w = \frac{1}{4}\dot\gamma_{aw}\left(3 + \frac{1}{n}\right).$$

Meanwhile, when n becomes 1, the shear rate for the Herschel-Bulkley model reduces to that of the Bingham plastic model, $$\dot\gamma_w = \dot\gamma_{aw}\frac{3}{(1-c)[(1-c)^2 + 2]} \qquad (38)$$

Thus, the shear rate can be determined from the shear stress at the same point (i.e., at the wall) in Equation 7. Therefore, the Herschel-Bulkley viscosity, $\eta_{HB}=K\dot\gamma_w^n$, can be directly related with the volume flow rate and pressure drop as follows:

$$\eta_{HB} = \frac{\tau_w - \tau_0}{\dot\gamma_w} = \frac{2\rho g R^4}{2LA_{riser}} \frac{n\beta}{(n+1)} \left(\frac{\Delta h(t) - \Delta h_\infty}{\frac{dh(t)}{dt}}\right) \qquad (39)$$

Meanwhile, the generalized Newtonian viscosity ($\eta$) of the Herschel-Bulkley fluid corresponding to the wall shear rate can also be determined from the measured quantity, h(t) as:

$$\eta = \frac{\tau_w}{\dot\gamma_w} = \frac{\pi\rho g R^4}{2LA_{riser}} \frac{n\beta}{(n+1)} \left[\frac{\Delta h(t)}{\frac{dh(t)}{dt}}\right] \qquad (40)$$

Furthermore, based on Equation 25, the yield stress $\tau_0$ is given by:

$$\tau_0 = \frac{\rho g \Delta h_\infty R}{2L} \qquad (41)$$

Figure 5:
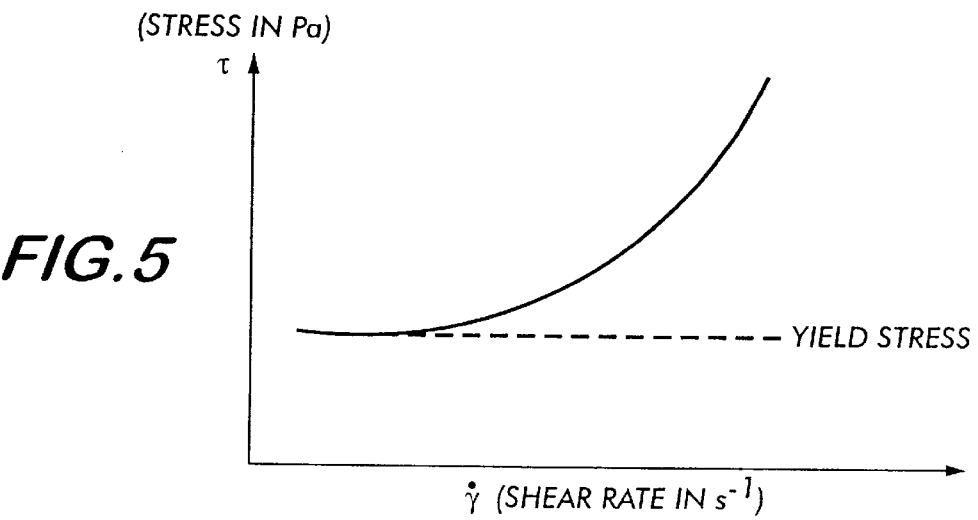
FIG. 5 is a shear stress vs. shear rate plot of the ER (or MR) fluid column in the riser tube R2.
Figure 6:
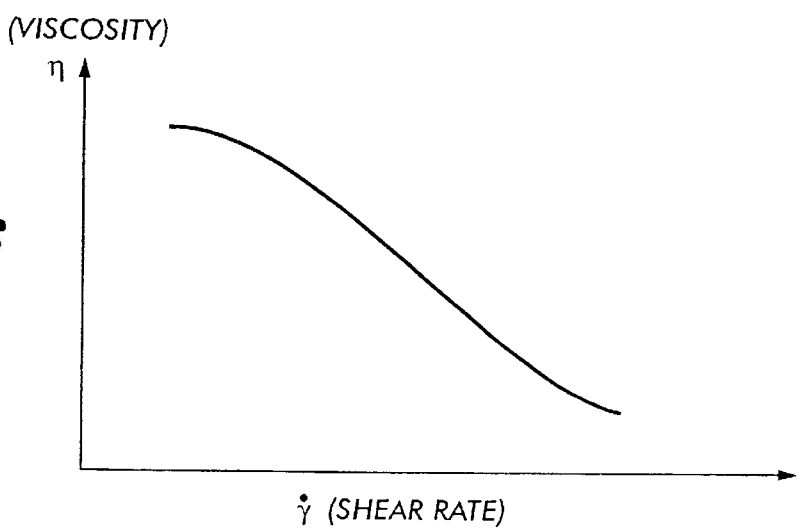
FIG. 6 is viscosity vs. shear rate plot of the ER (or MR) fluid column in the riser tube R2.

FIG. 4 depicts the fluid level variation, h(t), in the riser tube R2. FIG. 5 depicts the shear stress vs. shear rate characteristic and FIG. 6 depicts the fluid viscosity vs. shear rate characteristic.

As mentioned earlier, two ER fluids were analyzed: a cornstarch-corn oil mixture (15:85 by weight) and a zeolite-corn oil mixture (40:60 by weight).

Figure 7A:
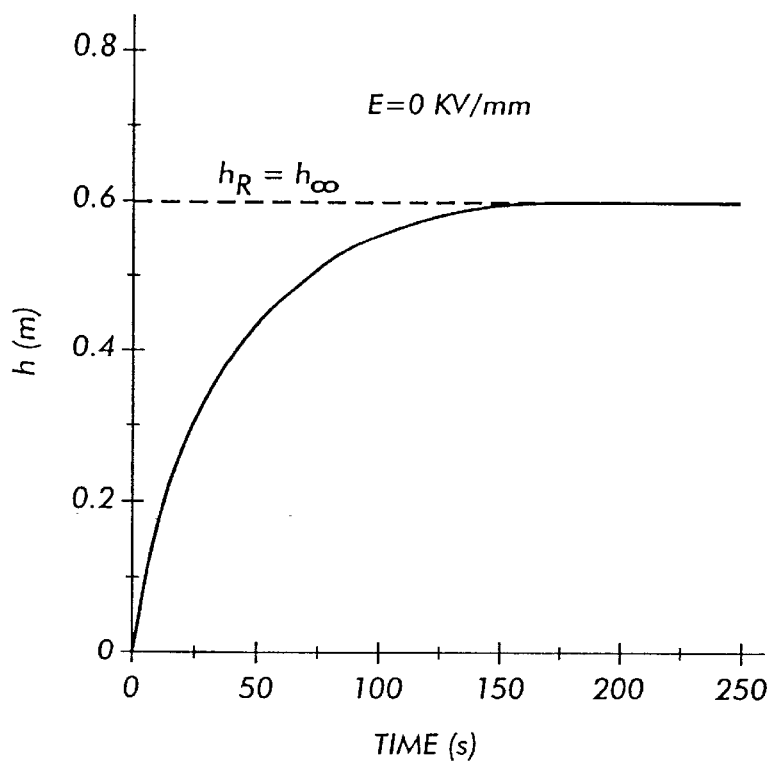
FIG. 7A is a height vs. time plot for a first test ER fluid (e.g., cornstarch-corn oil mixture) when a static/alternating electric field of 0 kV/mm was applied.
Figure 7B:
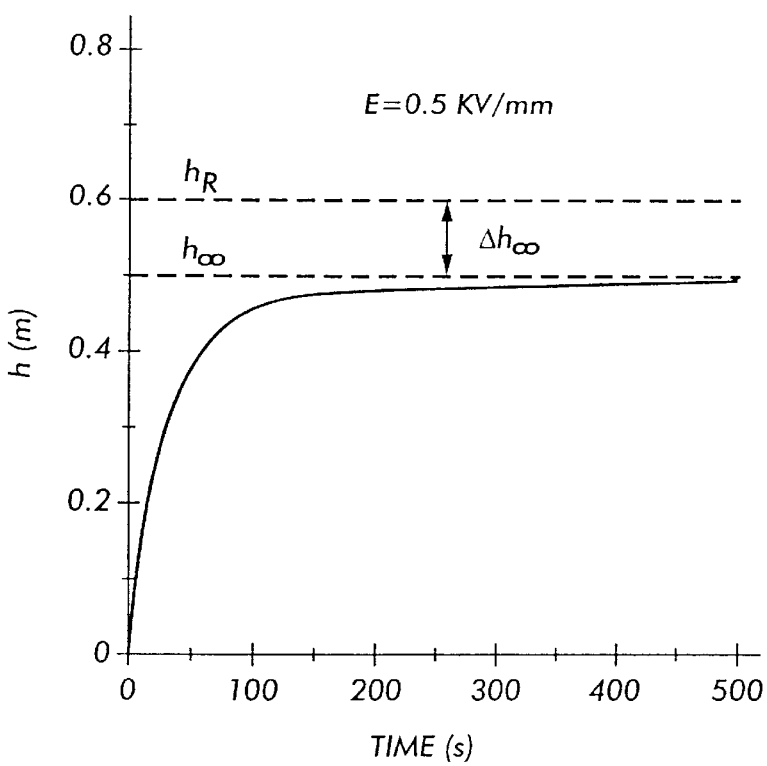
FIG. 7B is a height vs. time plot for the first test ER fluid when a static electric field of 0.5 kV/mm was applied.

FIG. 7A depicts the fluid level variation, h(t), in the riser tube R2 obtained with the cornstarch-corn oil mixture at room temperature with E=0 kV/mm and 0.5 kV/mm. As time passed beyond 200 seconds, the fluid level in the riser tube asymptotically reached a plateau value ($h_\infty$) which is the same as the fluid level, $h_R$, in the reservoir 22. In particular example, the height at t=176 seconds was 605 mm in FIG. 7A, whereas the height at t=216 seconds was 609 mm ($h_\infty$). This corresponds to $h_R$ which was also 609 mm. Next, applying a static/alternating electric field of 0.5 kV/mm, as shown in FIG. 7B, the plateau value, $h_\infty$, was determined to be much smaller than $h_R$, a phenomenon which can be attributed to the yield stresses ($\tau_0$) of the ER fluid. This phenomenon can be explained as follows: when an E field is applied to the ER fluid, it causes a transition of the ER fluid from a liquid state to a solid state at low shear rates, resulting in the yield stress of the ER fluid, and also resulting in a hydrostatic equilibrium even for non-zero pressure head difference between the reservoir 22 level and the riser tube R2 column. FIG. 8 shows the flow curve for the cornstarch-corn oil mixture without the influence of a static/alternating electric field. The ER fluid exhibited a Newtonian behavior as shown in FIG. 8. Moreover, the results obtained from the rheometer 20 showed good agreement with the conventional rotating viscometer's (e.g., Haake VT-550) result in the shear rate range. It should be noted that the rheometer 20 provides viscosity data in the low shear rate range as compared to the rotating viscometer.

Figure 9:
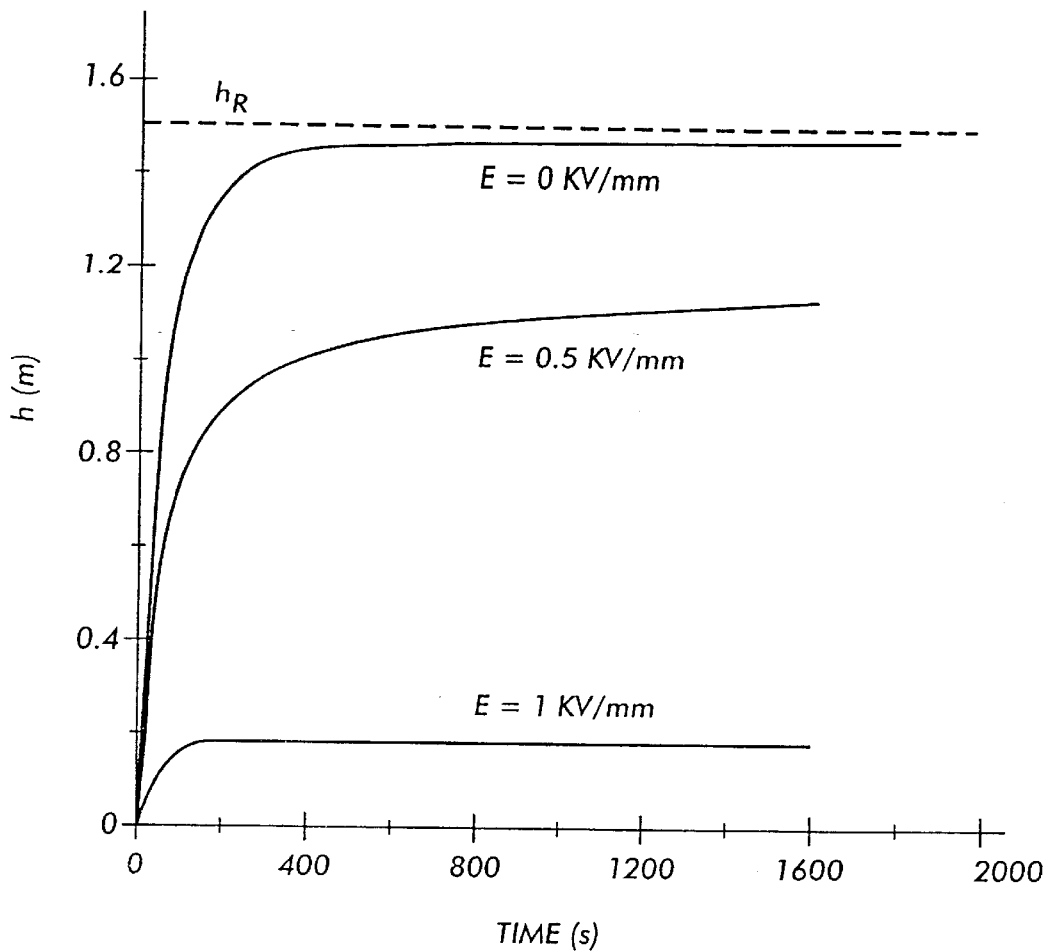
FIG. 9 are height vs. time plots for a second test ER fluid (e.g., zeolite-corn oil mixture) using electric fields of 0 kV/mm, 0.5 kV/mm and 1 kV/mm.

FIG. 9 depicts the fluid level variation, h(t), in the riser tube R2 obtained with the zeolite-corn oil mixture at room temperature with varying electric field (E) magnitudes. For E=0 kV/mm, as time passed beyond 800 seconds, the fluid level reached a plateau level, $h_\infty$, asymptotically. In particular, the height at t=800 seconds, was 1475 mm in FIG. 9, whereas the height at t=8000 seconds (not shown in FIG. 9) was 1480 mm. As shown in FIG. 9, at the end of the test run (t=∞), there remained a significant difference ($\Delta h_\infty$) between the initial fluid level, $h_R$, in the reservoir 22 and the final level of the column in the riser tube R2. As mentioned earlier with the cornstarch-corn oil mixture, this difference can be attributed to the yield stress ($\tau_0$) of the zeolite-corn mixture. Moreover, the rheometer's 20 test results demonstrated excellent agreement with those from the conventional rotating viscometer (Haake VT-550) over a range of shear rates (e.g., $10^1 \sim 10^3$ s$^{-1}$), including low shear rates.

It should be understood that the position of the flow restrictor 28 is not limited to the riser R1 but could be located as part of the transfer tube 29, or even located in the riser tube R2.

Figure 11:
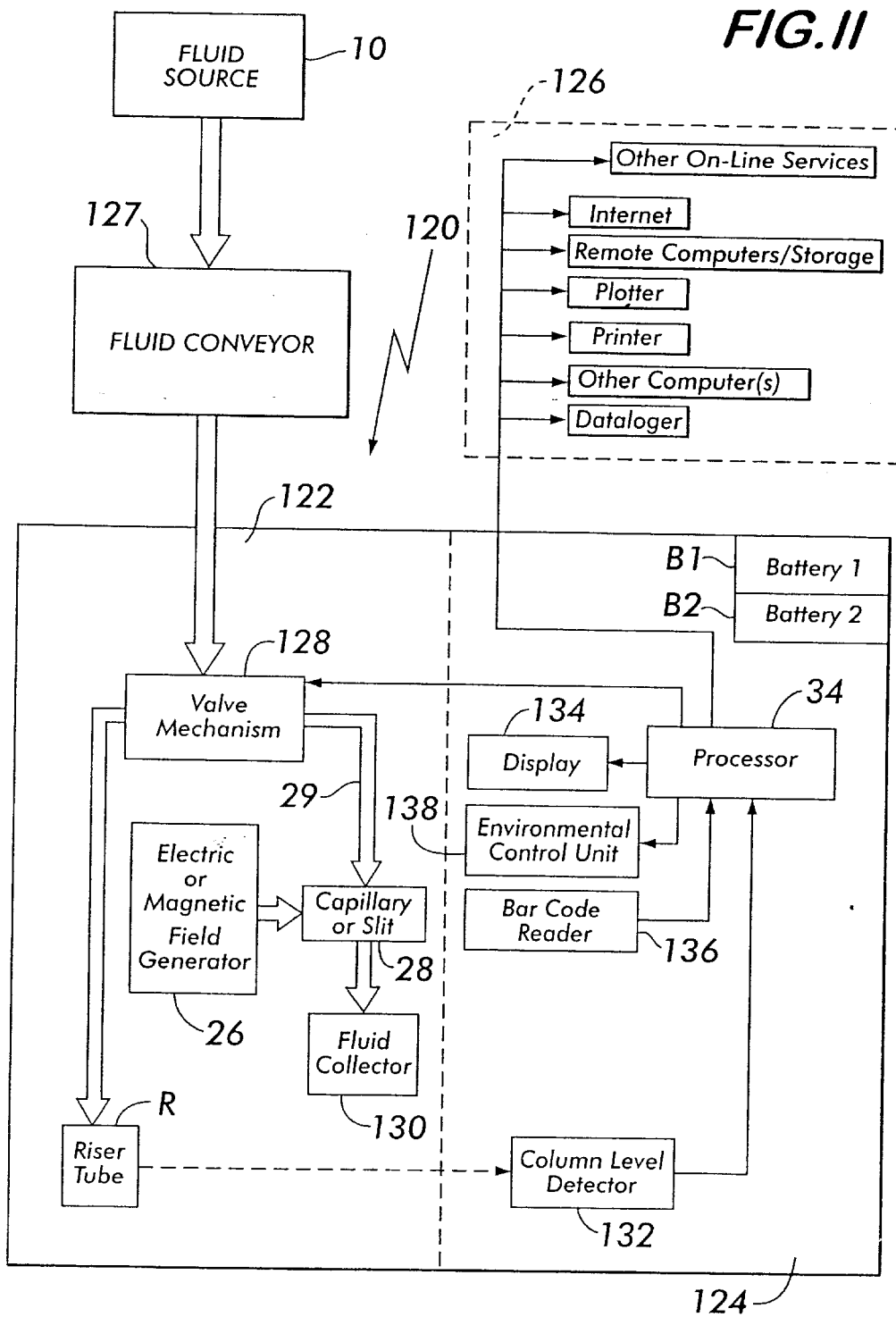
FIG. 11 is a block diagram of the rheometer apparatus coupled to either a static or dynamic source of ER or MR fluid which utilizes a falling column of fluid for viscosity determination.

In light of the above, the rheometer 20 can be used to determine the viscosity over a range of shear rates as well used to determine the yield stress of a variety of different fluids in an absolute zero rate range. FIG. 11 is a block diagram of the rheometer 120 of the present invention that can be coupled to either a static fluid source (e.g., the reservoir 22 of the rheometer 20 having a test fluid deposited therein) or a dynamic fluid source (e.g., the vascular system of a living being). For example, the yield stress of the circulating blood of a living being can be analyzed using the rheometer 120. Furthermore, unlike the rheometer 20, the rheometer 120 uses a falling column of fluid for the viscosity determination. However, the operation of the decreasing pressure differential is the same.

In particular, the rheometer 120 comprises a fluid receptor 122 and an analyzer 124. An output section 126 can be coupled to the analyzer 124 for providing the results to other peripheral devices (e.g., computers, plotters, printers, etc.) whether they are local or remote. Furthermore, where the fluid source 10 is dynamic (e.g., the vascular system of a living being), a fluid conveyor 127 (e.g., a needle, a catheter, etc.) couples the fluid source 10 to the fluid receptor 122.

The fluid receptor 122 comprises a valve mechanism 128, a riser tube R, the electric field generator, or magnetic field generator, 26, the flow restrictor 28 (comprising either the slit 28A or the capillary tube 28B), the transfer tube 29 and a fluid collector 130. In this configuration, it should be noted that the flow restrictor 28 forms a portion of the transfer tube 29 rather than forming a portion of the riser tube R as shown earlier. Furthermore, it should be noted that the riser tube R can be positioned at any angle greater than zero degrees with respect to the horizontal reference position, e.g., $h_\infty$; in FIG. 13A, this angle is 90°.

As mentioned earlier, the electric field generator 26 may comprise any power supply capable of generating E fields in the 10 kV/mm range and that the magnetic field generator 26 may comprise any conventional magnetic field generators for generating magnetic fields in the range of 100–1000 Gauss, including any of the configurations shown in FIGS. 2D–2G;

these coil configurations may be coupled to a function generator and amplifier that can generate an alternating electric/magnetic field where both the magnitude and frequency can be varied.

The fluid collector 130 comprises any receptacle for collecting that fluid that exits the riser tube R after the test run. This collector 130 may be disposable, as is the valve mechanism 128, the flow restrictor 28, the transfer tube 29 and the riser tube R where the fluid under test is a bio-fluid (e.g., blood).

Figure 13A:
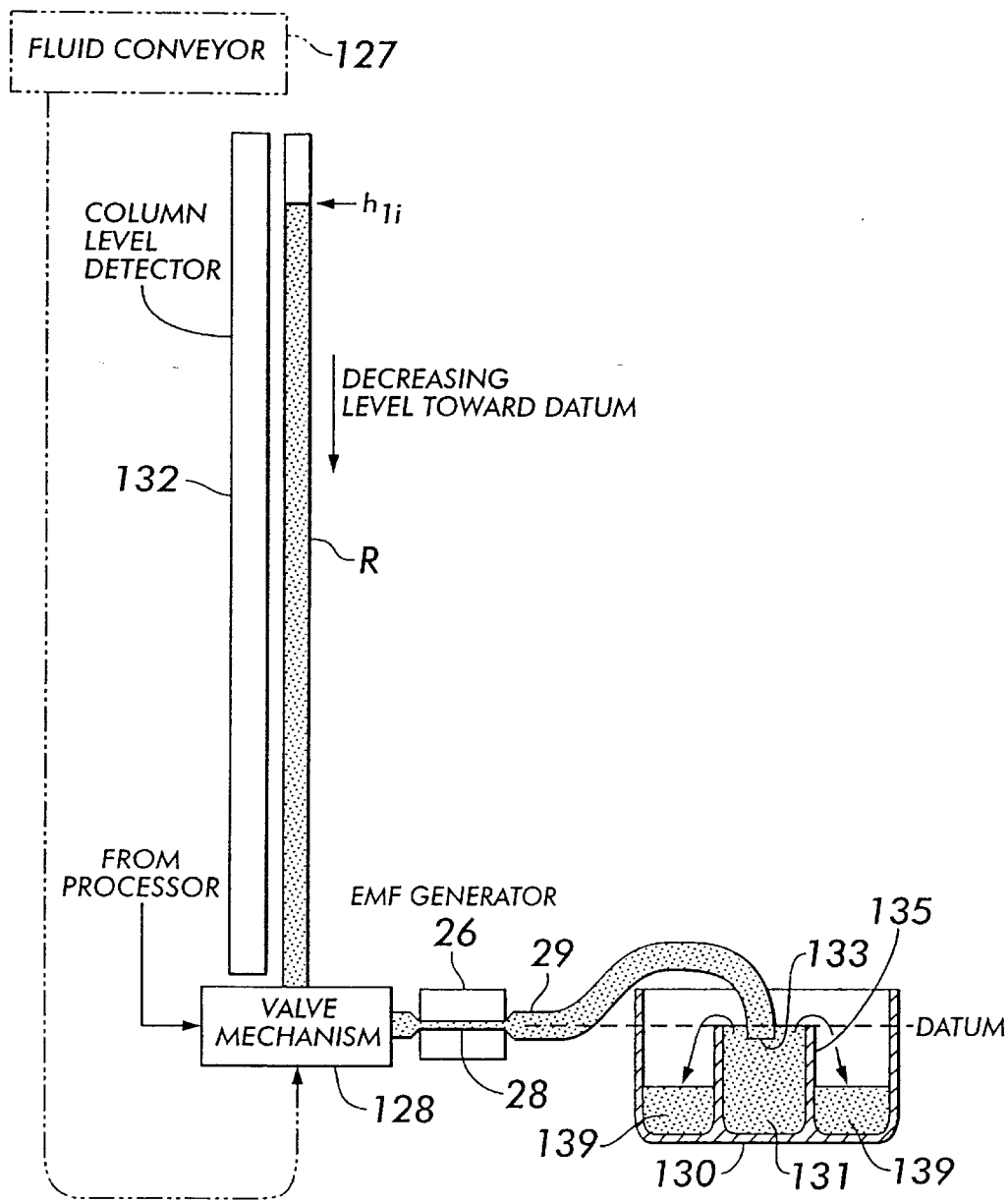
FIG. 13A is an operational diagram of the first embodiment of the ER/MR fluid scanning rheometer with the flow restrictor forming a part of the transfer tube.

The fluid collector 130 as shown most clearly in FIG. 13A comprises an inner circular wall 135 that divides the collector 130 into a central portion 131 and an annular portion 139. The central portion 131 receives the far end, or outlet, 133 of the transfer tube 29, which, during the test run, remains submerged under the fluid level to minimize any surface tension effects. As the fluid fills the collector 130, the fluid 24 can spill over the top of the inner circular wall 135 while maintaining the outlet 133 of the transfer tube 29 submerged.

The analyzer 124 comprises the processor 34, a column level detector 132, a display 134, a bar code reader 136, an environmental control unit 138, and a first battery B1 and a second back-up battery B2. The column level detector 132 monitors the level of blood in the riser tube R. The processor 34 (e.g., a "386" microprocessor or greater, or any equivalent) is arranged to analyze the data from the detector 132 and calculate the viscosity and yield stress therefrom. Furthermore, the processor 34 also controls the display 134 for providing the viscosity/yield stress information and the other information to the operator as well as to the output section 126. The processor 34 also controls the valve mechanism 128 based on the data from the detector 132, as will be discussed later. Battery B1 provides all of the requisite power to the analyzer 124, with battery B2 serving as a back-up power supply. It should be understood that power for the electric field generator, or the magnetic field generator, 26 is not supplied from the batteries B1/B2, but requires an external source. The bar code reader 136 provides an automated manner in which the details of the flow restrictor 28/riser tube R can be automatically fed to the processor 34 for viscosity/yield stress analysis. The environmental control unit 138 (e.g., a heater, fan and/or thermostat) can be used where the fluid under test is a temperature-dependent fluid (e.g., circulating blood of a living being) and the fluid needs to be maintained at the living being's body temperature throughout the test run.

Figure 12:
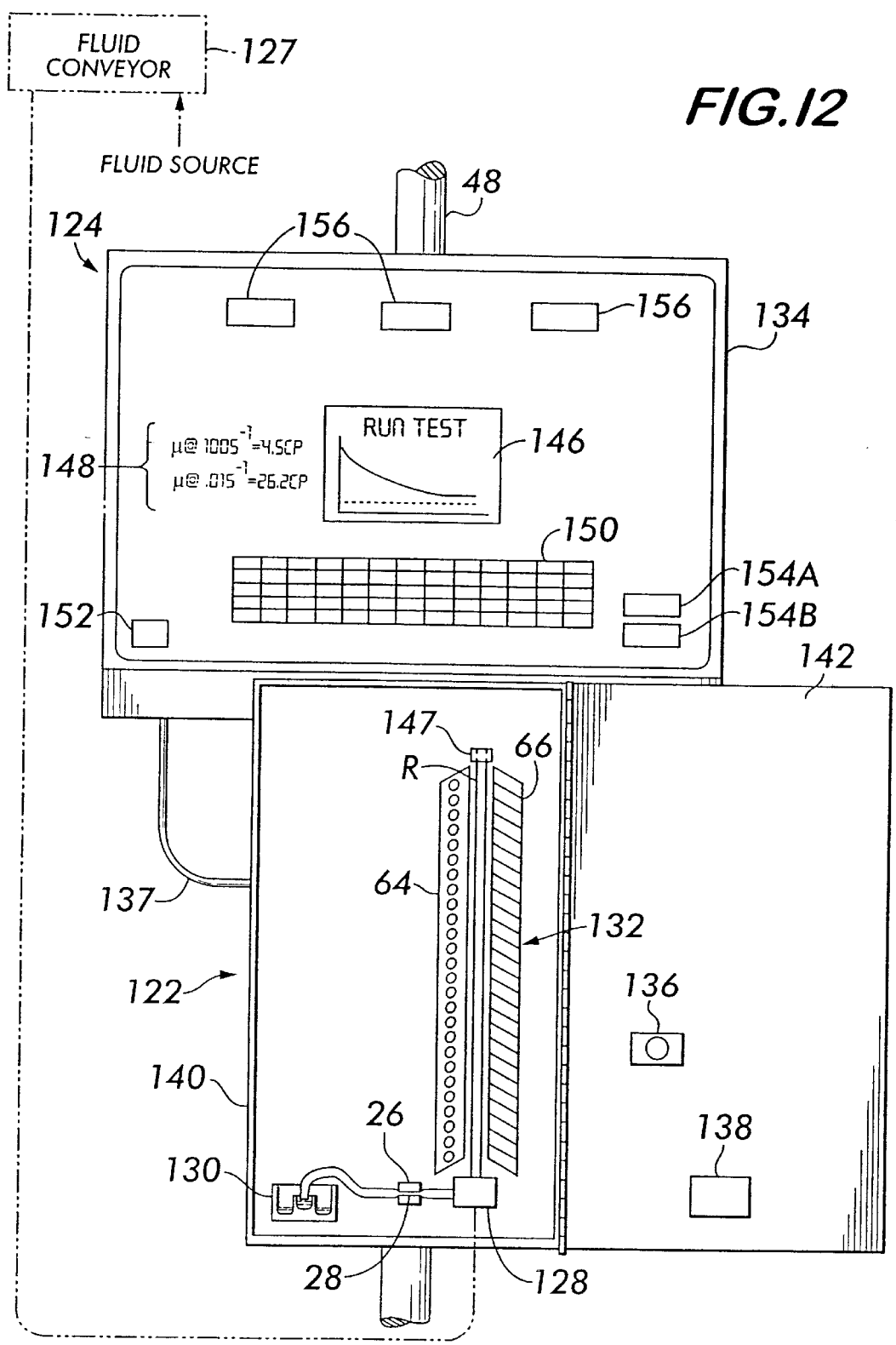
FIG. 12 is a front view of one embodiment of the ER/MR fluid scanning rheometer apparatus, showing a display and a housing with its door in an opened condition which houses the column level detector.

As shown more clearly in FIG. 12, a first embodiment of the rheometer 120 comprises a fluid receptor housing 140 having a door 142. The housing 140 contains the riser tube R, the detector 132, the valve mechanism 128, the flow restrictor 28, the collector 130, the electric (or magnetic) field generator 26, the bar code reader 136 and the environmental control unit 138. The door 142 permits the operator to gain access to the fluid receptor components, especially in those scenarios where the components are disposable. For example a bracket 147 may be used to releasably secure the upper portion of the riser tube R. The column level detector 132 is preferably not removable from the housing 140. Once the components are inserted, the rheometer 120 is ready for testing, and the door 142 is closed to provide a dark environment for the detector 132. The detector 132 may comprise any conventional level detector, e.g., an LED (light emitting diode) array 64 and a CCD (charge coupled device) 66 located on opposite sides of the riser tube R, as discussed in A Ser. No. 09/439,795, which is incorporated by reference herein and therefore will not be repeated here.

It should be understood that, although not shown, an electric/magnetic (EMF) shield surrounds the generator 26/flow restrictor 28 to shield the detector 132, as well as the analyzer 124, from the effects of the electric or magnetic field during activation.

The display 134 may comprise any suitable conventional device, e.g., an ELD (electroluminescent display) or LCD (liquid crystal display) that permits the visualization of both text and graphics. The resolution of this display 28 is preferably 800×600 VGA or above. Furthermore, while the preferred embodiment utilizes a touch screen display which incorporates, among other things:

graphical display 146 instruction, and/or data, display 148 (which also includes the command line display shown as "RUN TEST"; e.g., "TESTING", "TEST IN PROGRESS," etc.)

alphanumeric keypad 150 emergency stop button 152 battery status indicators, 154A and 154B function buttons 156.

It should be understood that any equivalent display device is within the broadest scope of the invention. Thus, any number of user interfaces and buttons may be available through the display 134. Therefore, the rheometer 120 is not limited to the embodiment that is shown in FIG. 12. Moreover, the display 134 can be operated to minimize or maximize, or overlay any particular graphic or text screen, as is available in any conventional object-oriented operating system, such as Microsoft® WINDOWS. Furthermore, the processor 34 may be located in the same housing as the display 134. A wire harness 137 electrically couples the display 134/ processor 34 to the detector 132 and valve mechanism 128.

Figure 13B:
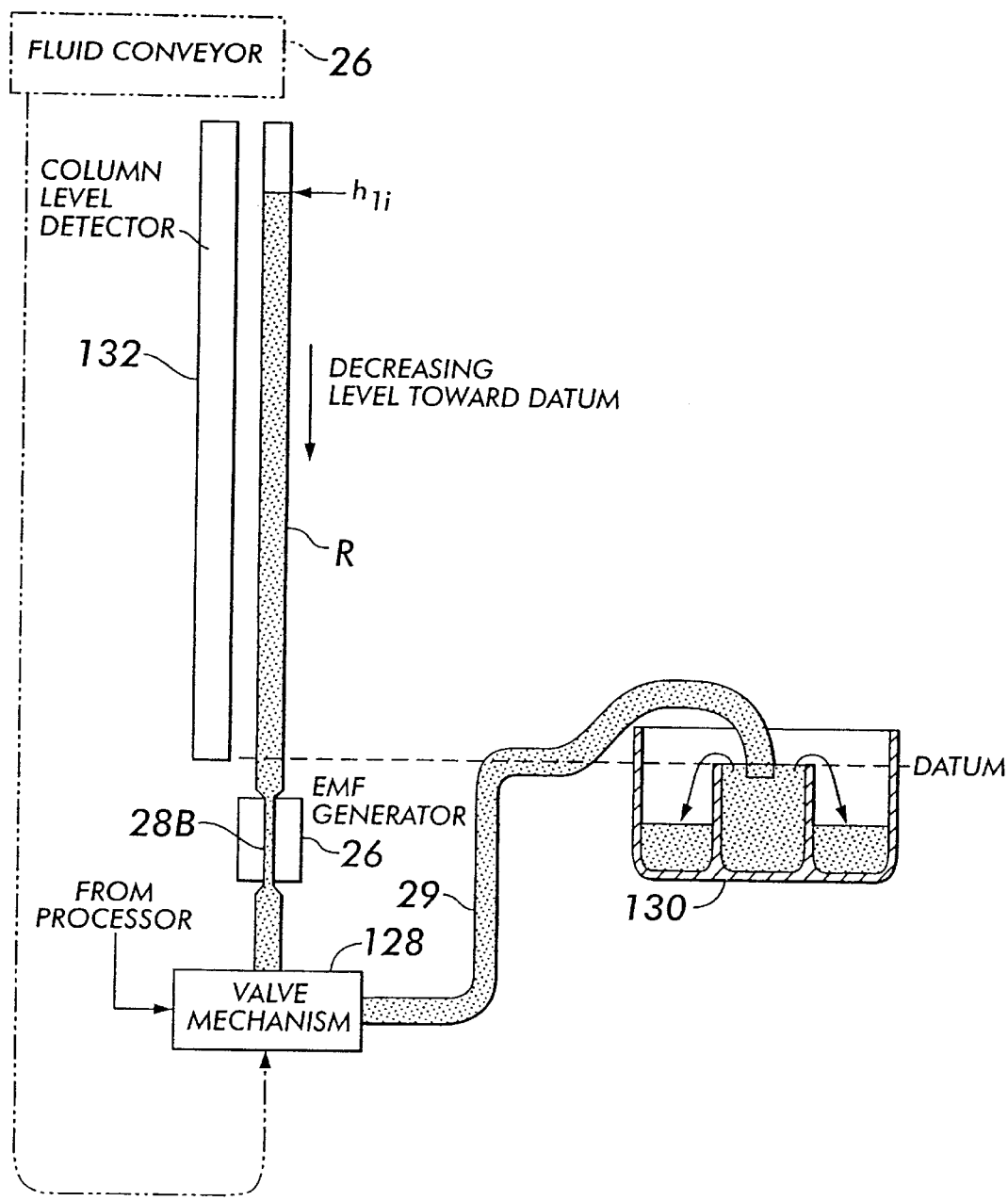
FIG. 13B is an operational diagram of the first embodiment of the ER/MR fluid scanning rheometer with the flow restrictor forming a part of the riser tube.

FIGS. 13A and 13B provide enlarged views of the rheometer 120 operation but with the flow restrictor 28 located in different fluid receptor 122 components. In particular, in FIG. 13A, the flow restrictor 28 forms a portion of the transfer tube 29 whereas in FIG. 13B, the flow restrictor 28 forms a portion of the riser tube R. In either case, operation of the rheometer 120 is similar.

FIGS. 13C–13D provide the sequence of the valve mechanism 128 operation as controlled by the processor 34. In particular, the valve mechanism 128 may comprise a stop cock valve 158 and a valve driver 160 (e.g., 500 mA solenoid, or step motor, etc.) such as that disclosed in A Ser. No. 09/439,795, which is incorporated by reference herein. The fluid conveyor 26 is coupled to the valve mechanism 128 at a port 153; the flow restrictor 28 is coupled to the valve mechanism 128 at a port 155; and the riser tube R is coupled to the valve mechanism 128 at a port 157. When the rheometer 120 is coupled to the fluid source 10 via the fluid conveyor 26, the processor 34 commands the valve driver 160 to rotate the valve 158 such that fluid flow is upward from the fluid conveyor 26 into the riser tube R (FIG. 13A). The detector 132 monitors the rise of the column level in the riser tube R. When a predetermined column level is detected, the detector 132 informs the processor 34 which commands the valve driver 160 to rotate the valve 158 to the position shown in FIG. 13B. As the fluid flows down the riser tube R, the processor 34 then energizes the electric field, or magnetic field, generator 26 to alter the fluid viscosity. The detector 132 monitors the falling column of fluid as it flows downward and through the flow restrictor 28.

Figure 14A:
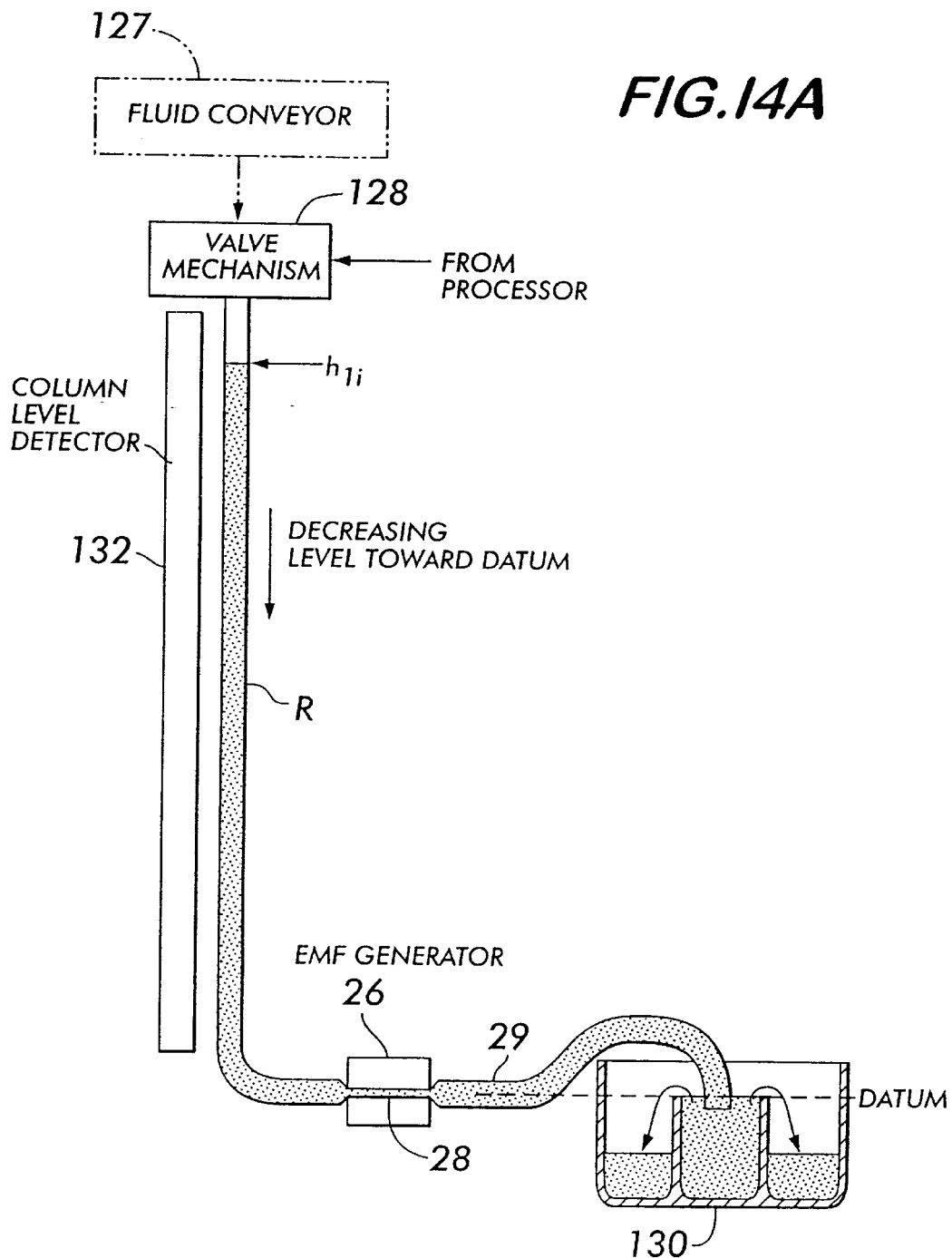
FIG. 14A is an operational diagram of the second embodiment of the ER/MR fluid scanning rheometer where the valve mechanism is located at the top of the riser tube.
Figure 14B:
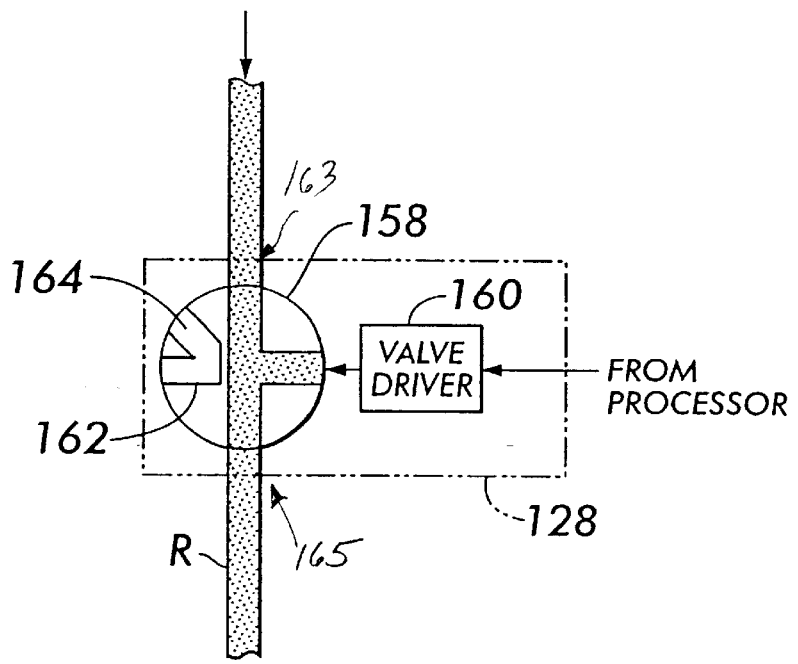
FIGS. 14B–14C depict the valve mechanism operation during the test run of the second embodiment.
Figure 14C:
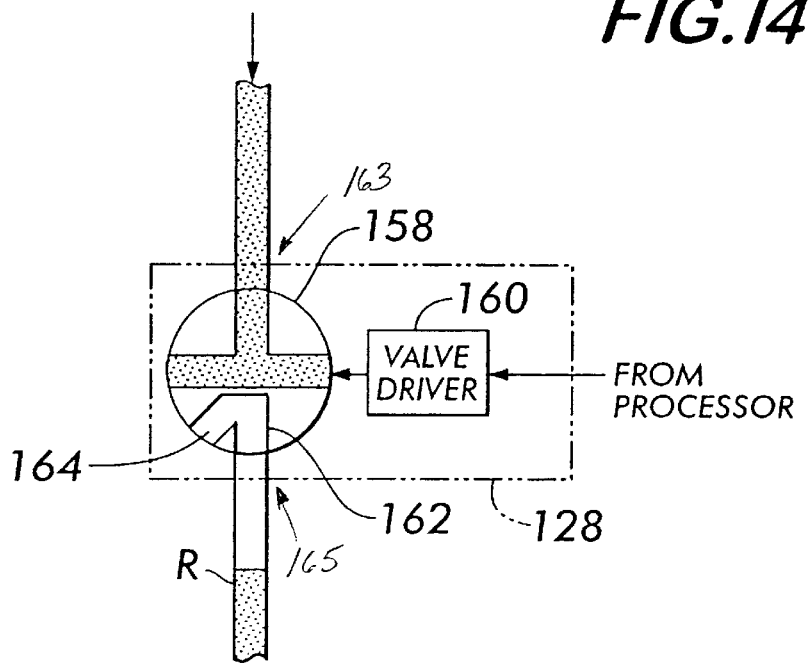

FIG. 14A depicts an enlarged view of the rheometer 120 operation but with the valve mechanism 128 located at the top of riser tube R. The advantage of this valve mechanism 128 position is that there is no need to first fill the riser tube R to a predetermined level before proceeding with the test run; instead, in accordance with the valve mechanism 128 operation as shown in FIGS. 14B–14C, the test run proceeds with the processor 34 commanding the valve driver 160 to rotate the valve 158 to the position shown in FIG. 14B and then the processor 34 stops any more input flow from the fluid conveyor 26 as shown in FIG. 14C. In particular, as used in this embodiment, the fluid conveyor 26 is coupled to the valve mechanism 128 at a port 163; the top end of the riser tube R is coupled to the valve mechanism 128 at a port 165. The valve mechanism 128 also includes a vent coupler 162 that couples the top of the riser R to third port 164 that is exposed to atmospheric pressure; thus when the valve 158 is rotated into the position shown in FIG. 14C, the fluid in the riser tube R will flow downwards.

The viscosity determination and the yield stress determination using the rheometer 120 utilize the same mathematical principles discussed earlier for the rheometer 20 and therefore will not be repeated here. Thus, the viscosity and yield stress profiles (FIGS. 5–6) would be the same for the rheometer 120. The only difference is that instead of using a rising column of fluid as does the rheometer 20, the rheometer 120 uses a falling column. Therefore, it is within the broadest scope of this invention to include the use of either a rising or a falling column of fluid.

Figure 12A:
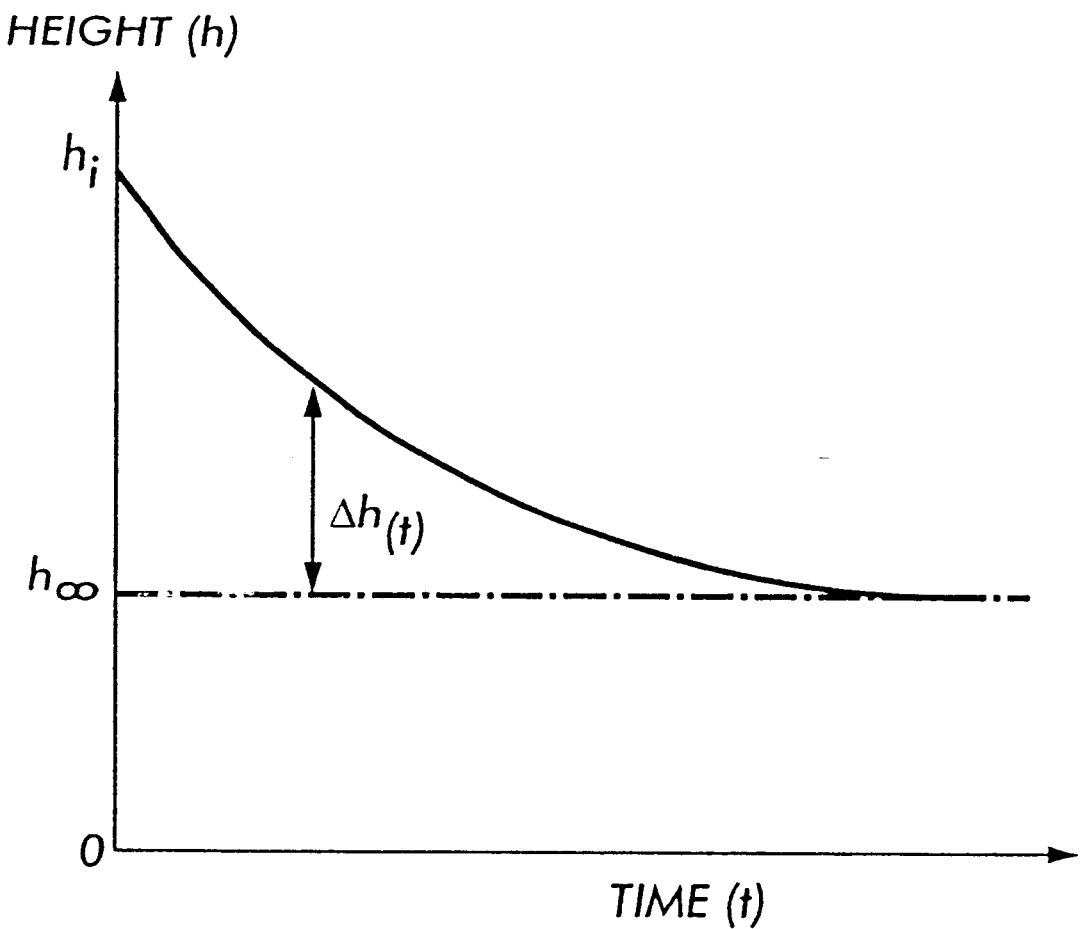
FIG. 12A is a height vs. time plot based on the rheometer of FIG. 12.

As a result of using a falling column, the definition of $\Delta h(t)$ and $\Delta h_\infty$ are defined as shown in FIG. 12A, where $h_\infty$ is defined as the centerline of the flow restrictor 28, or as the top level of the central portion 131 in the fluid collector 130.

Without further elaboration, the foregoing will so fully illustrate our invention and others may, by applying current or future knowledge, readily adapt the same for use under various conditions of service.

We claim:

1. An apparatus for determining the viscosity of a fluid over plural shear rates using a decreasing pressure differential, said apparatus comprising:

a fluid source elevated at a first reference position above a horizontal reference position;

a flow restrictor having a first end and a second end, said first end being in fluid communication with the fluid source, said flow restrictor having some known dimensions;

a lumen having one end in fluid communication with said second end of said flow restrictor and another end being exposed to atmospheric pressure, said lumen having a portion positioned at an angle greater than zero degrees with respect to said horizontal reference position, and wherein a pressure differential exists between a column of fluid in said portion and said elevated fluid source, said column of fluid moving through said flow restrictor and said lumen at a first shear rate caused by said pressure differential, said movement of fluid causing said pressure differential to decrease from said first shear rate for generating said plural shear rates;

a sensor for detecting the movement of said column of fluid, said sensor generating data relating to the movement of said column of fluid over time;

an electric/magnetic field generator for subjecting said flow restrictor to an electric/magnetic field when the fluid is flowing therein; and a processor, coupled to said sensor, for calculating the viscosity of the fluid over a range of plural shear rates based on said data relating to the movement of the column of fluid over time and said some known dimensions.

2. The apparatus of claim 1 wherein said electric/magnetic field generator comprises an electric field generator for generating a static electric field or an alternating electric field and wherein the fluid is an electrorheological fluid.

3. The apparatus of claim 1 wherein said electric/magnetic field generator comprises a magnetic field generator for generating a static magnetic field or an alternating magnetic field and wherein the fluid is a magnetorheological fluid.

4. The apparatus of claim 3 wherein said flow restrictor comprises a capillary tube that is subjected to a static magnetic field, or an alternating magnetic field with respect to time, when the fluid is flowing therethrough.

5. The apparatus of claim 4 wherein said portion of said lumen is a riser tube that is positioned vertically with respect to said horizontal reference position and wherein said movement of fluid forms a rising column of fluid, said sensor monitoring the movement of said rising column.

6. The apparatus of claim 1 wherein said sensor comprises a light array and a charge coupled device.

7. The apparatus of claim 6 wherein said light array comprises a plurality of light emitting diodes arranged in linear fashion to illuminate said portion of said lumen along the length of said portion of said lumen.

8. A method of determining the viscosity of a fluid over plural shear rates using a decreasing pressure differential, said method comprising the steps of:

(a) elevating a fluid source above a horizontal reference position to establish a pressure differential between said fluid source and said horizontal reference position;

(b) placing one end of a flow restrictor in fluid communication with the fluid source and wherein said flow restrictor comprises some known parameters;

(c) placing a second end of said flow restrictor in fluid communication with one end of a lumen and wherein a second end of said lumen is exposed to atmospheric pressure;

(d) positioning said lumen at angle greater than zero degrees with respect to said horizontal reference position;

(e) allowing the fluid to flow from said fluid source through said flow restrictor and said lumen, thereby decreasing said pressure differential which causes the fluid to experience a plurality of shear rates;

(f) applying an electric/magnetic field to said flow restrictor as the fluid flows through said flow restrictor;

(g) detecting the movement of the fluid through said lumen over time to generate data relating to the movement of the fluid through said lumen; and (h) calculating the viscosity of the fluid over a range of shear rates based on said data and said some known parameters.

9. The method of claim 8 wherein said electric/magnetic field is a static electric field or an alternating electric field and wherein the fluid is an electrorheological fluid.

10. The method of claim 8 wherein said electric/magnetic field comprises a static magnetic field or an alternating magnetic field and wherein the fluid is a magnetorheological fluid.

11. The method of claim 10 wherein said flow restrictor comprises a capillary tube that is subjected to a static magnetic field, or an alternating magnetic field, when the fluid is flowing therethrough.

12. The method of claim 11 wherein said lumen comprises a riser tube that is positioned vertically with respect to said horizontal reference position and wherein said movement of fluid forms a rising column of fluid, said sensor monitoring the movement of said rising column.

\* \* \* \* \*